(12) United States Patent
Gibbard et al.

(10) Patent No.: US 11,696,841 B2
(45) Date of Patent: Jul. 11, 2023

(54) PROSTHETIC LIMBS

(71) Applicant: Open Bionics Ltd, Bristol (GB)

(72) Inventors: Joel Gibbard, Bristol (GB); Jonathan Raines, Bristol (GB); Samantha Payne, Bristol (GB); Steve Wood, Wiltshire (GB)

(73) Assignee: Open Bionics Ltd, Bristol (GB)

( * ) Notice: Subject to any disclaimer, the term of this patent is extended or adjusted under 35 U.S.C. 154(b) by 0 days.

(21) Appl. No.: 16/368,678

(22) Filed: Mar. 28, 2019

(65) Prior Publication Data

US 2019/0298551 A1 Oct. 3, 2019

Related U.S. Application Data

(60) Provisional application No. 62/649,914, filed on Mar. 29, 2018.

(51) Int. Cl.
| | |
|---|---|
| *A61F 2/78* | (2006.01) |
| *A61F 2/80* | (2006.01) |
| *A61F 2/58* | (2006.01) |
| *A61F 2/70* | (2006.01) |
| *A61F 2/72* | (2006.01) |
| A61F 2/76 | (2006.01) |
| A61F 2/54 | (2006.01) |
| A61F 2/60 | (2006.01) |
| A61F 2/30 | (2006.01) |
| A61F 2/50 | (2006.01) |

(52) U.S. Cl.
CPC .......... *A61F 2/7812* (2013.01); *A61F 2/582* (2013.01); *A61F 2/583* (2013.01); *A61F 2/585* (2013.01); *A61F 2/586* (2013.01); *A61F 2/70* (2013.01); *A61F 2/72* (2013.01); *A61F 2/78* (2013.01); *A61F 2/80* (2013.01); *A61F 2/54* (2013.01); *A61F 2/60* (2013.01); *A61F 2/76* (2013.01); *A61F 2002/30505* (2013.01); *A61F 2002/5001* (2013.01); *A61F 2002/543* (2013.01); *A61F 2002/587* (2013.01)

(58) Field of Classification Search
CPC ........ A61F 2/7812; A61F 2/582; A61F 2/583; A61F 2/585; A61F 2/586; A61F 2/70; A61F 2/72; A61F 2/76; A61F 2/78; A61F 2/80; A61F 2/54; A61F 2/60; A61F 2002/30505; A61F 2002/5001; A61F 2002/543; A61F 2002/587; A61F 2002/5026; A61F 2/68; A61F 2002/546; A61F 2002/5083; A61F 2002/7881; A61F 2002/701; A61F 2002/704; A61F 2002/6854; A61F 2002/5027; B33Y 10/00; B33Y 80/00; B29C 64/118; A61G 2002/5018
USPC ........................................................... 623/61
See application file for complete search history.

(56) References Cited

U.S. PATENT DOCUMENTS 3,459,179 A 8/1969 Olesen
9,155,636 B1 * 10/2015 Fikes ................... A61F 2/7812
(Continued)

FOREIGN PATENT DOCUMENTS

| EP | 0182412 A1 | 5/1986 |
| EP | 0346697 A1 | 12/1989 |
| EP | 0363654 A2 | 4/1990 |

*Primary Examiner* — Jerrah Edwards
*Assistant Examiner* — Aren Patel
(74) *Attorney, Agent, or Firm* — Lightbulb IP, LLC

(57) ABSTRACT

An outer frame for a prosthetic limb is provided. The outer frame is formed from one or more parts and has a plurality of air flow openings.

20 Claims, 28 Drawing Sheets

(56) References Cited

U.S. PATENT DOCUMENTS

| | | | |
|---|---|---|---|
| 10,238,511 B1* | 3/2019 | Newton | A61F 2/80 |
| 2007/0225824 A1* | 9/2007 | Einarsson | A61F 2/80 |
| | | | 623/36 |
| 2010/0070051 A1* | 3/2010 | Carstens | A61F 2/80 |
| | | | 623/34 |
| 2010/0161076 A1 | 6/2010 | Pallari | |
| 2010/0312359 A1* | 12/2010 | Caspers | A61F 2/80 |
| | | | 623/34 |
| 2015/0265432 A1* | 9/2015 | King | A61F 2/80 |
| | | | 623/34 |
| 2016/0296345 A1* | 10/2016 | Deshpande | A61F 2/586 |
| 2017/0049583 A1* | 2/2017 | Belter | A61F 2/72 |
| 2017/0216056 A1* | 8/2017 | Hill | A41D 27/06 |
| 2017/0281368 A1* | 10/2017 | Gill | A61F 2/585 |
| 2019/0175363 A1* | 6/2019 | Wu | A61F 2/585 |

* cited by examiner

PROSTHETIC LIMBS

The present invention relates generally to prosthetic limb and particularly, although not exclusively, to a robotic prosthetic arm.

A prosthesis is an artificial device that replaces a missing body part, which may be lost through trauma, disease, or congenital conditions. Prosthetics are intended to restore the normal functions of the missing body part.

The present invention seeks to provide improvements in or relating to prosthetic limbs.

An aspect of the present invention provides an outer frame for a prosthetic limb, the outer frame being formed from one or more parts and having a plurality of air flow openings.

According to a further aspect of the present invention there is provided a prosthetic limb comprising an outer frame, the outer frame having a plurality of airflow openings.

The limb may further comprise an inner socket. The inner socket may have a plurality of airflow openings In some embodiments the present invention provides or relates to a transradial prosthesis—an artificial limb that replaces an arm missing below the elbow. In other embodiments the present invention provides a transhumeral prosthesis—a prosthetic lower and upper arm, including a prosthetic elbow.

In some embodiments the present invention provides or relates to a myoelectric prosthesis, which uses the electrical tension generated every time a muscle contracts, as information.

The outer frame may have a lattice or lattice-like structure, such as an open core lattice structure. This provides strength whilst at the same time inherently providing ventilation.

The socket, where present, may have a plurality of longitudinal flutes. The socket may, therefore, have a generally cylindrical and "concertina-like" configuration. This allows, for example, the socket to be expandable and compressible. Vent holes may be formed in the flutes.

The socket may be flexible. The flexibility may be provided by material choice and/or structural form.

In some embodiments the frame can be tensioned on to or around the socket. The frame may be relatively rigid and the socket may be relatively flexible so that tightening of the frame can tension the socket to provide a good fit onto the patient.

The frame may comprise attachment points for a removable cover. In some embodiments magnets are used to attached removable covers.

In some embodiments the frame is formed a one piece. In other embodiments the frame is formed from two or more sections.

In some embodiments the socket is formed from two sections.

The outer frame and/or inner socket may be formed by an additive manufacturing method, such as 3D printing. In some embodiments the or each part of the outer frame is formed by selective laser sintering.

The present invention also provides a robotic prosthetic arm, comprising a ventilated outer frame and a ventilated inner liner.

The present invention also provides a prosthetic arm comprising an outer frame and an inner socket, the outer frame having attachment points for receiving a removable cover.

The outer frame may be formed from a first and a second frame portion. A removable cover portion may be provided, a first cover portion being attachable to the first frame portion and a second cover portion being attachable to the second frame portion.

The frame may include integral cover attachment points, for example pads with Velcro® or other such releasable fastener (such as a magnet) that can engage corresponding attachment zones on a cover to ensure the cover is correctly received.

Limbs, such as arms and arm structures, formed in accordance with the present invention may further comprise a wrist/ankle mechanism or the like and/or a hand/foot or the like.

The present invention also provides an inner socket/liner for a prosthetic limb, comprising one or more vents (such as vent holes/openings).

The present invention also provides a prosthetic limb, such as an arm or leg, comprising a ventilated outer frame and a ventilated inner liner.

The limb may further comprise a removable cover portion.

Example Constraints for Aspects and Embodiments

An 'umbrella' constraint for the arm is that the user should be happy to wear it for a whole day.

Further examples of broad device-wide constraints are summarized below.

Weight

The unit should be lightweight. Being lighter than a human arm is not necessarily acceptable as many amputees will have become accustomed to not having that mass on the end of their residual limb.

Weight Distribution

It is not enough to simply reduce the overall weight of the device. Consideration should be paid to where the Centre of Mass (CoM) is located. The further from the elbow it is the more tiring the device is to wear.

Battery Life

The device should last a day at least. Everything from the battery selection, to the electronics design, to the mechanical design has been designed to allow a portable battery to provide enough energy for a day's use.

Aesthetics

Any device designed to be worn should take into account aesthetics. Many highly functional, desirable wearable devices have failed commercially because they failed to take this into account.

Risks

The arm is a relatively low risk device; indeed it is a Class 1 medical device under the Medical Device Directive (MDD) 93/42/EEC. If it fails, the user is not left immobile.

The device is in contact with the skin for extended periods of time. Therefore, there are biocompatibility concerns. Any materials in contact with the skin for extended periods will be independently tested to ISO 10993.

Furthermore, the circuitry of the device is in direct contact with the skin through the metal contacts of the EMG sensors. Protection circuitry is built in to protect the wearer from any faults, and the device is certified to the relevant parts of BS EN 60601. A removable, low-voltage battery power supply is used and cannot be charged in-situ, minimizing the possibility of any dangerous voltages reaching the user.

Different aspects and embodiments of the invention may be used separately or together.

Further particular and preferred aspects of the present invention are set out in the accompanying independent and dependent claims. Features of the dependent claims may be combined with the features of the independent claims as appropriate, and in combination other than those explicitly set out in the claims.

BRIEF DESCRIPTION OF THE DRAWINGS

The present invention will now be more particularly described, by way of example, with reference to the accompanying drawings, in which.

DEFINITIONS

Figure 1:
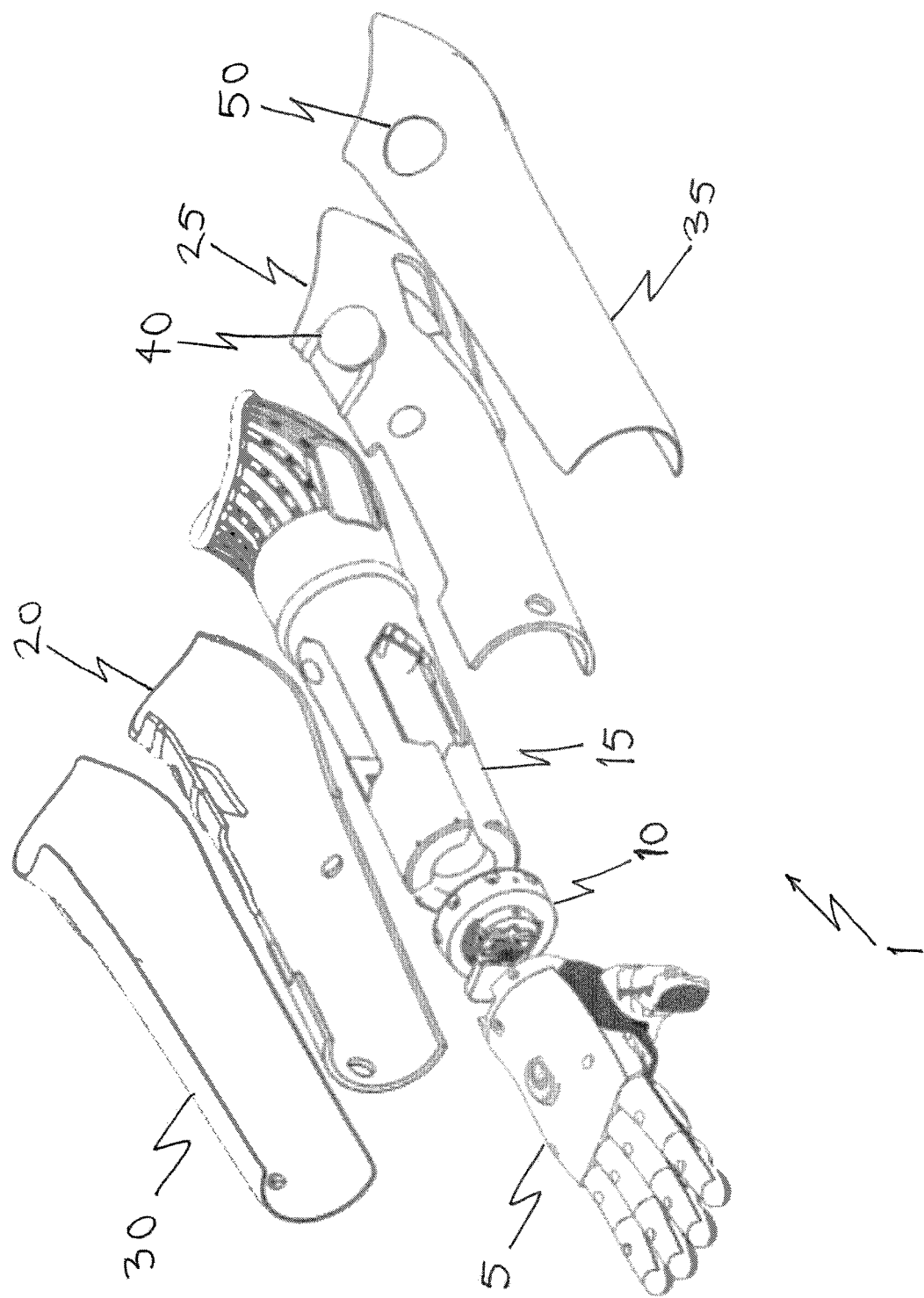
FIG. 1—exploded view of a prosthetic arm formed according to an embodiment.

Palmar—the side of something closest to the palm.

Axial Plane—the plane defined by a normal running axial to the object in question. If no object is specified, it should be assumed the term is being used in the broader anatomical way where the axial vector runs from head to foot through the body.

CoM—Centre of Mass $G^2$—Geometric continuity in the 2nd derivative. Two curves, meet at a point, share a tangent and curvature.

DFMEA—Design Failure Modes Effects Analysis

PCB—Printed Circuit Board

Example embodiments are described below in sufficient detail to enable those of ordinary skill in the art to embody and implement the systems and processes herein described. It is important to understand that embodiments can be provided in many alternate forms and should not be construed as limited to the examples set forth herein.

Accordingly, while embodiments can be modified in various ways and take on various alternative forms, specific embodiments thereof are shown in the drawings and described in detail below as examples. There is no intent to limit to the particular forms disclosed. On the contrary, all modifications, equivalents, and alternatives falling within the scope of the appended claims should be included. Elements of the example embodiments are consistently denoted by the same reference numerals throughout the drawings and detailed description where appropriate.

The terminology used herein to describe embodiments is not intended to limit the scope. The articles "a," "an," and "the" are singular in that they have a single referent, however the use of the singular form in the present document should not preclude the presence of more than one referent. In other words, elements referred to in the singular can number one or more, unless the context clearly indicates otherwise. It will be further understood that the terms "comprises," "comprising," "includes," and/or "including," when used herein, specify the presence of stated features, items, steps, operations, elements, and/or components, but do not preclude the presence or addition of one or more other features, items, steps, operations, elements, components, and/or groups thereof.

Unless otherwise defined, all terms (including technical and scientific terms) used herein are to be interpreted as is customary in the art. It will be further understood that terms in common usage should also be interpreted as is customary in the relevant art and not in an idealized or overly formal sense unless expressly so defined herein.

Referring first to FIG. 1, there is shown a prosthetic arm 1 designed to fit transradial amputees. It is comprised of three main sub-assemblies; the hand 5; the wrist 10; and the socket 15. The socket 15 is covered by an outer frame, which in this embodiment comprises a first frame part 20 and a second frame part 25. Additionally, optional, swappable covers 30, 35 can be added to style the arm.

The system is actuated by motors concealed within the hand palm. It is powered by a battery located, for example, either just below the elbow or inside the distal end of the arm. The user controls the system by flexing the muscles of their forearm; the system senses these flexes with Electromyographic (EMG) sensors embedded in the socket.

The arm is designed to offer amputees a level of functionality close to more advanced devices such as the BeBionic v3 from Otto Bock and the i-Limb from Touch Bionics, whilst still being affordable.

Mechanical Design

Hand

In this embodiment the hand contains the actuators and the main control PCB. Although this places a large proportion of the mass far from the elbow, it means the hand can be fitted to a wide range of transradial amputees. Any hardware placed between the end of the user's residual limb and the wrist limits the range of residual limbs that can be fitted. Amputees with an intact wrist would have a disproportionately long prosthetic arm.

In this embodiment the humanoid hand has four fingers and a thumb. It comes in left and right variants, and a variety of sizes.

Some embodiments use a three motor actuator block. In this arrangement, the outer two motors are used to flex the fingers by pulling on a tendon. Motor one flexes the first and second fingers, motor two flexes the thumb, and motor three flexes the third and fourth fingers. For larger hands, there is space to fit a four motor variant of the actuator block. In this case, the first and second fingers are actuated independently. Motor one flexes the first finger, motor two the second finger, motor three is linked to the thumb, and motor four flexes the third and fourth fingers. In this manner, hands with the four motor variant are capable of more dexterous grip patterns such as pinching.

Wrist

Attachment Interfaces

Figure 2:
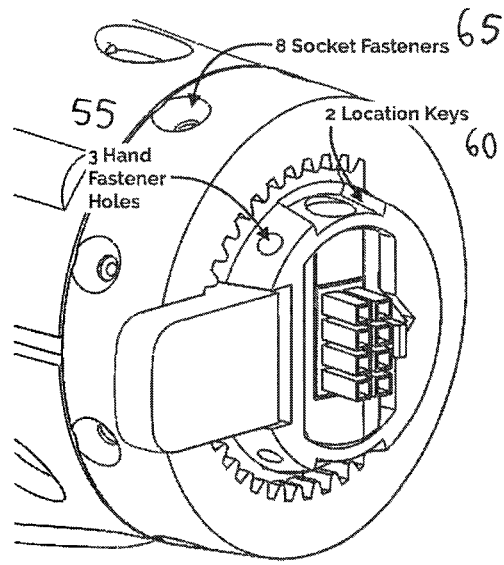
FIG. 2—shows the attachment of the hand to the wrist mechanism.

FIG. 2 illustrates the attachment of the wrist to the inner socket and the hand to the wrist mechanism.

In this embodiment attachment of the hand to the wrist is semi-permanent via three screws radially positioned and received in fastener holes 55. The screws can be removed along with the hand for maintenance.

The radial torque from the socket to the hand is transmitted via two keys (location keys, 60) so that the radial screws are disassociated and are just providing a pull-off constraint putting the screws in shear which is their strongest property.

Attachment of the wrist to the socket is via eight radial self-tapping fasteners 65 that screw into the Cheetah-based material of the socket liner, again the screws are in shear which is utilising their strongest property to resist pull-off loads. The Cheetah material is semi flexible and will heavily resist vibration related unfastening.

Rotating Mechanism

Figure 3:
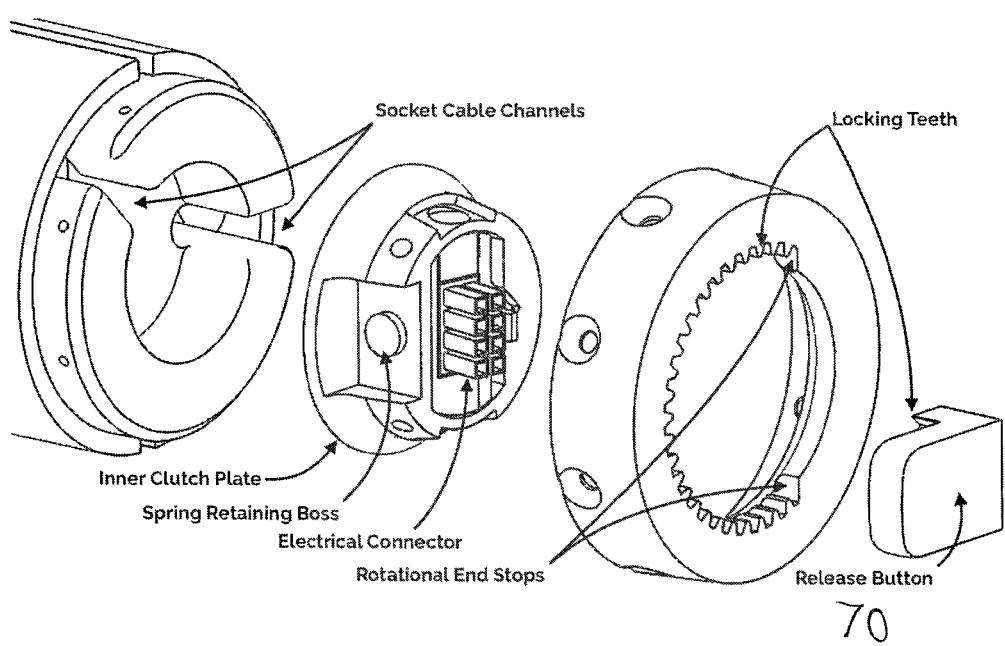
FIG. 3—Sub-components of the wrist mechanism.

FIG. 3 shows the sub-components of the wrist mechanism. The wrist has been designed to rotate the hand+/−90 deg ° from a neutral position. The neutral position has been defined as the hand in the vertical plane with the thumb upwards. Therefore the hand can be indexed to the palm up or palm down position.

The wrist rotation is naturally locked with a button 70 on the dorsal side of the wrist requiring to be depressed to unlock. Depression of the button releases internal gear teeth allowing indexing of the hand at approximately 7° increments. A spring forces the teeth on the button back into place locking the wrist upon release. There are different (for example two) sizes of wrist diameters, each use the same internal components and mechanism, only the outside diameter and release button length is modified.

Cable Management

In this embodiment the wrist has to allow pass through of both power and EMG signal cables between the hand and the socket components. Because the locking and index mechanism is low profile, an 8-pin connector has been incorporated into the central space, which connects to the hand's main board upon hand fitment. Behind this connector, there is space for a spiral wrap of cables which will expand and contract as the wrist rotates. At the distal end of the socket, the cables will split into two different feeds, one for the EMG circuit on and one for the battery pack. In this embodiment the length of the wrist section is 20 mm and diameters are, for example, 56 mm (large) and 46 mm (small).

Arm

Socket

In this embodiment the socket/liner is printed in the semi flexible Cheetah plastic from Fenner Drives which is a certified medical safe material to ISO 10993, tested by Envigo Laboratory.

Due to the socket's flexibility and design profile, it is both expandable and compressible which allows some growing room and an element of conformality to the user's residual arm shape.

Adjustability of the fit comes from the external panels compressing on the outer surface of the socket via a cable tensioning system.

Figure 4:
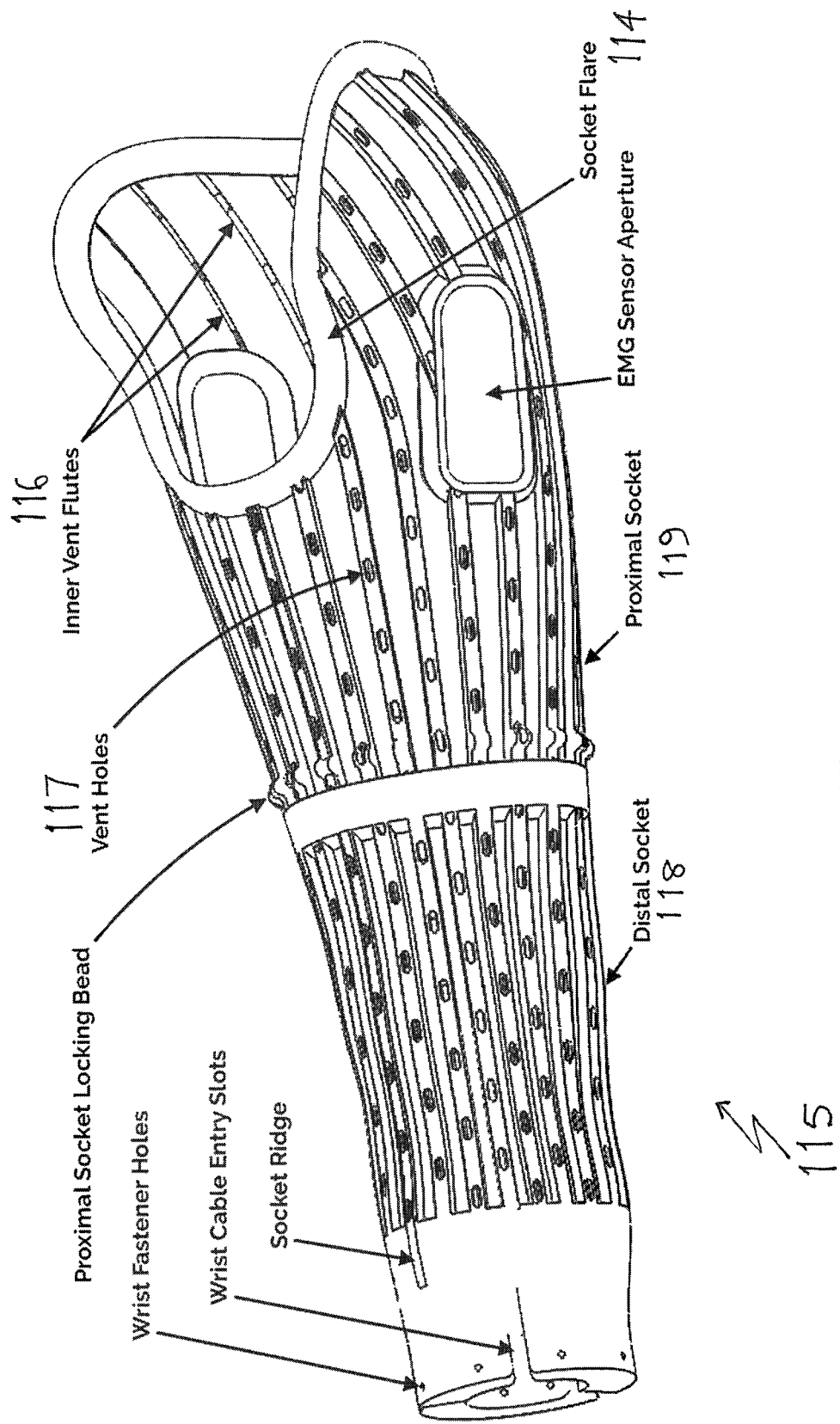
FIG. 4 shows the various features of a socket.

FIG. 4 shows the various features on a socket 115 formed according to an embodiment of the present invention. Ventilation is achieved due to the fluted nature of the socket where small air channels have been incorporated, the fluted channels 116 are printed with holes 117 to allow heat and moisture to escape externally and allow fresh air to permeate through to the skin. As discussed below, in this embodiment the covering frames are also aerated via a mesh like structure which helps reduce heat containment.

Figure 5:
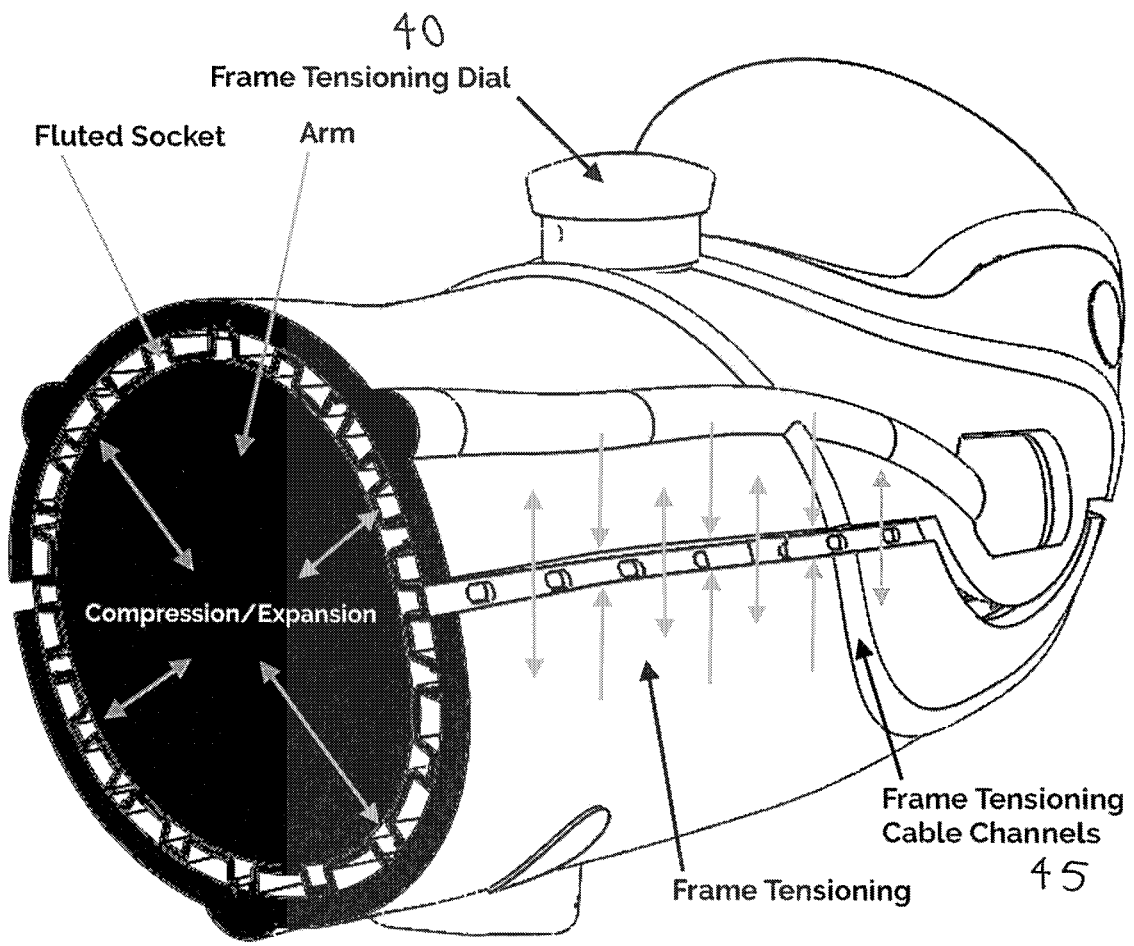
FIG. 5 shows how covering frames compress on the flutes of the socket via a tensioning system.

FIG. 5 shows how the covering frames compress on the flutes via a tensioning system and due to the thin walled nature of the flutes, the socket adjusts its diameter to conform to a range of shapes. A frame tensioning 40 dial and frame tensioning cables 45 are provided. FIG. 1 shows that the cover 35 has a hole 50 for the dial 40.

In this embodiment the socket is printed in two parts, a fixed distal socket section 118 which is attached to the wrist via the eight socket fasteners described in FIG. 2 and a removable proximal socket section 119 that can be washed and cleaned easily. In other embodiments the socket is formed as a one-piece article; or in other embodiments a socket made from two section split longitudinally may be formed.

The double section socket also makes the 3D printing process of some embodiments more stable by reducing the need to print tall slender flexible objects. The proximal section of the socket is held in place by a locking bead feature which is captivated by the outer frames coupled with a cable tensioning system.

For each patient the optimum EMG sensor position should be attained. The socket has cutouts shaped so that sensor assembly can be pushed through from the outside to achieve fitment against the skin at the desired location.

Figure 6:
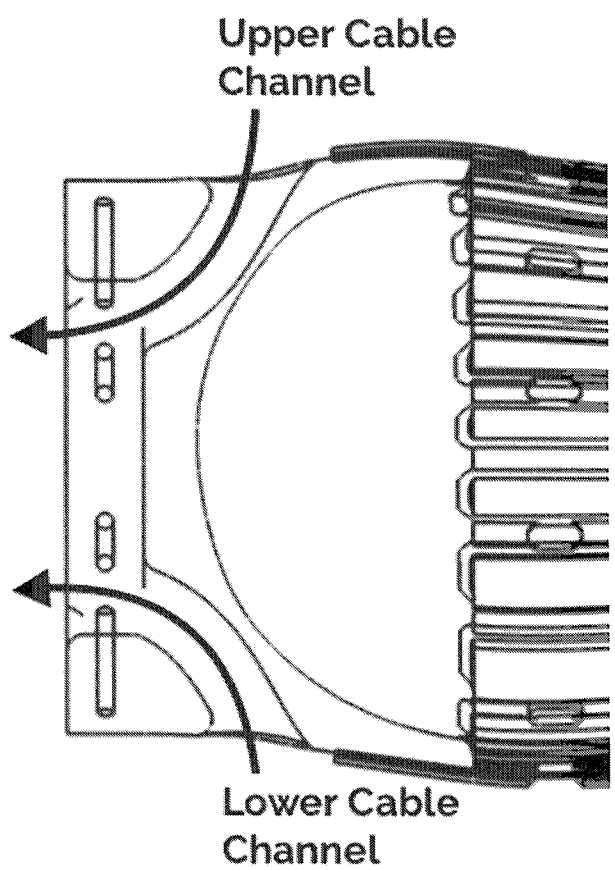
FIG. 6—Cable entry/exit channels.

Cable management has to pass through from the outside of the arm, through the outer frames and socket into the wrist. The distal end of the socket has channels for the EMG and battery power cables to pass through as shown in FIG. 6.

The flared entry 114 around the elbow is extended to cover the epicondyle areas to achieve some clamp and prevent the socket from falling off. During the scan rectification phase, these areas can be reworked to give extra clamp. These areas on the clamping frames can also be reworked with heat at the patient fitment phase. Running along the length of the socket are location ridges for the outer frames, this is to stop any radial slip during the tightening process with a cable tensioning system.

Thermoformed Frames

External to the socket are two frames that provide an adjustable clamping force to retain the socket on the arm.

There are currently two configurations of the arm, which impacts the shape of the frames.

Figure 7:
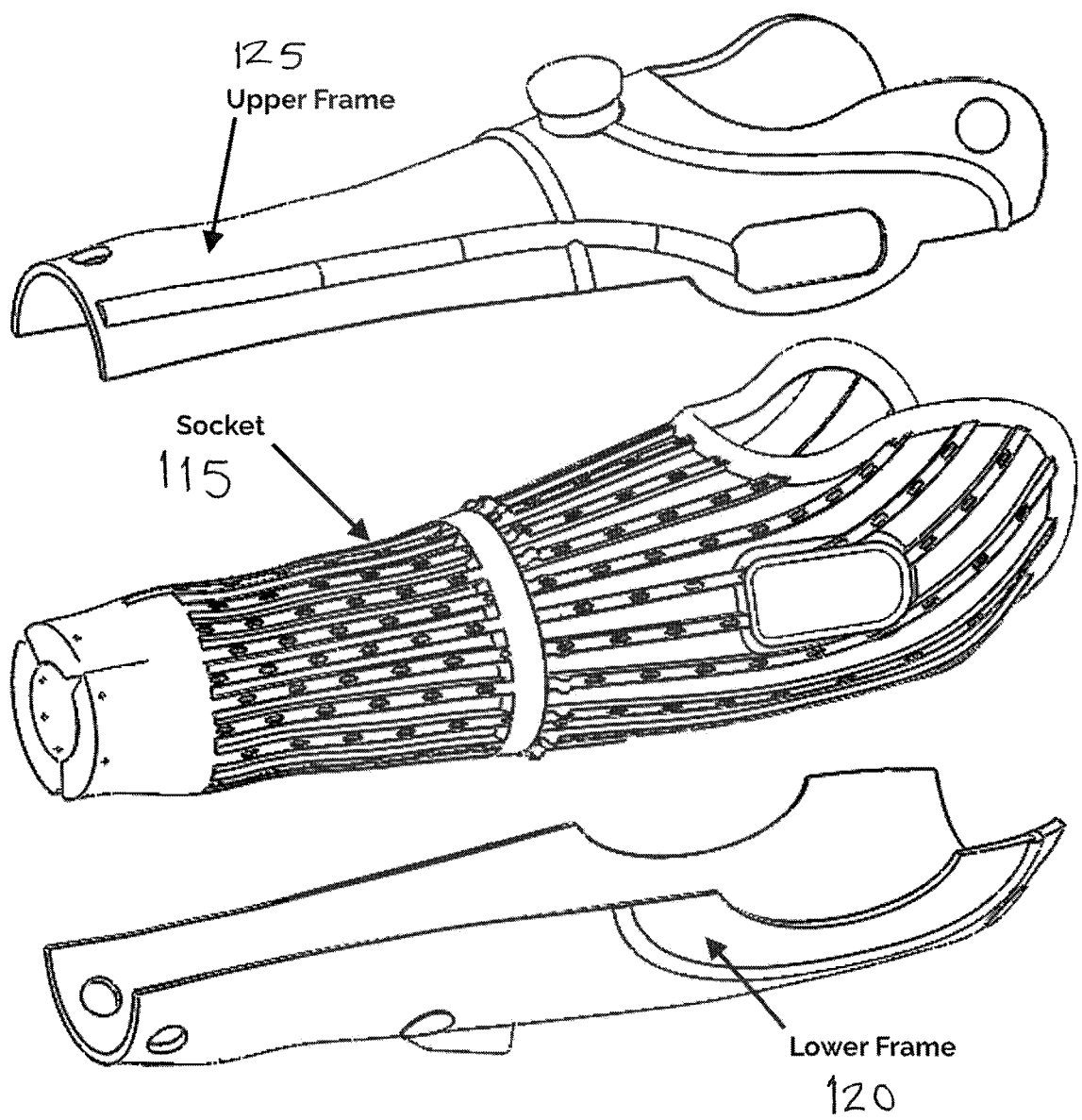
FIG. 7—Upper and Lower Clamping Frame Configuration.
Figure 8:
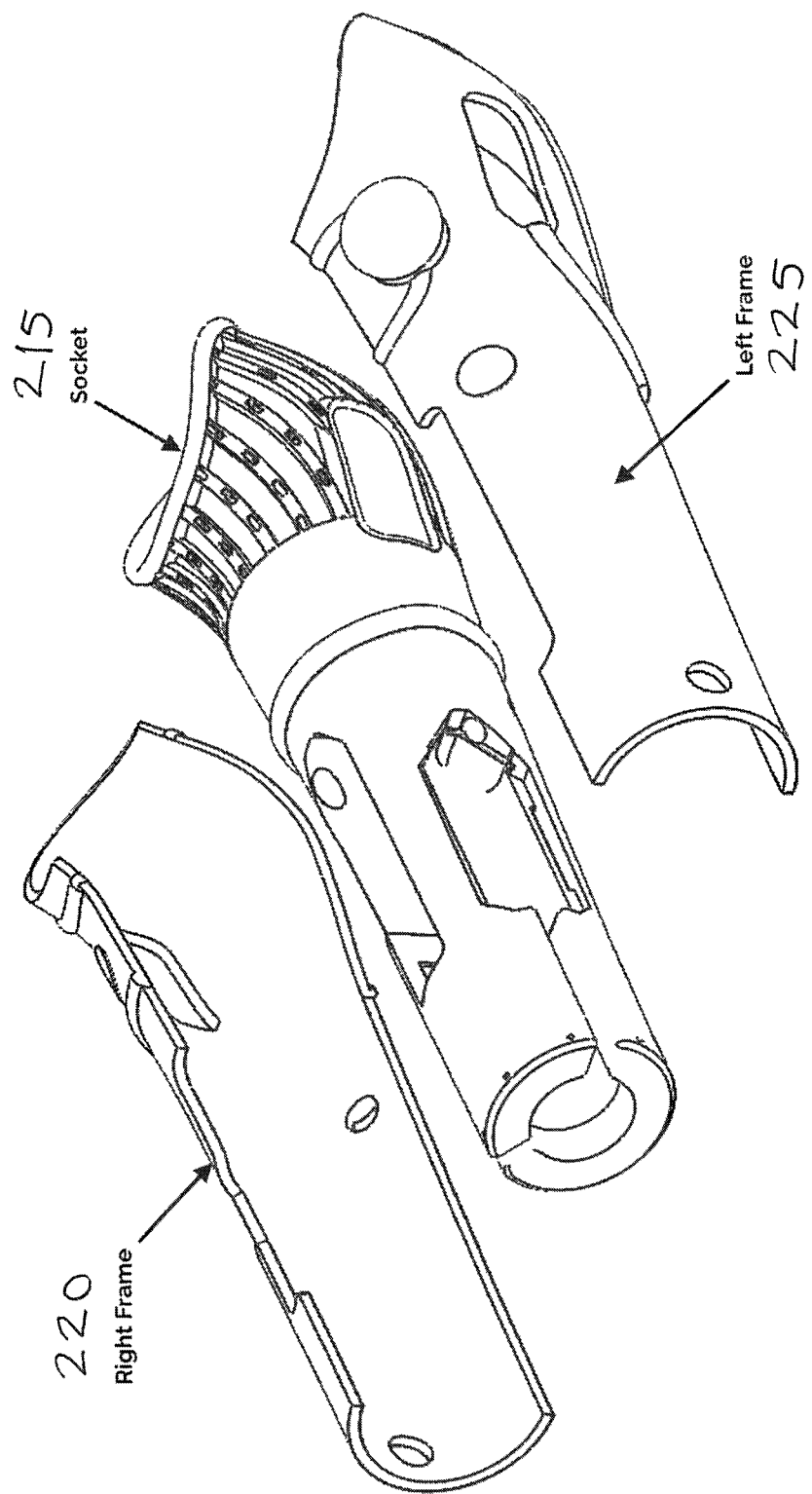
FIG. 8—Left and Right Clamping Frame Configuration.
Figure 9:
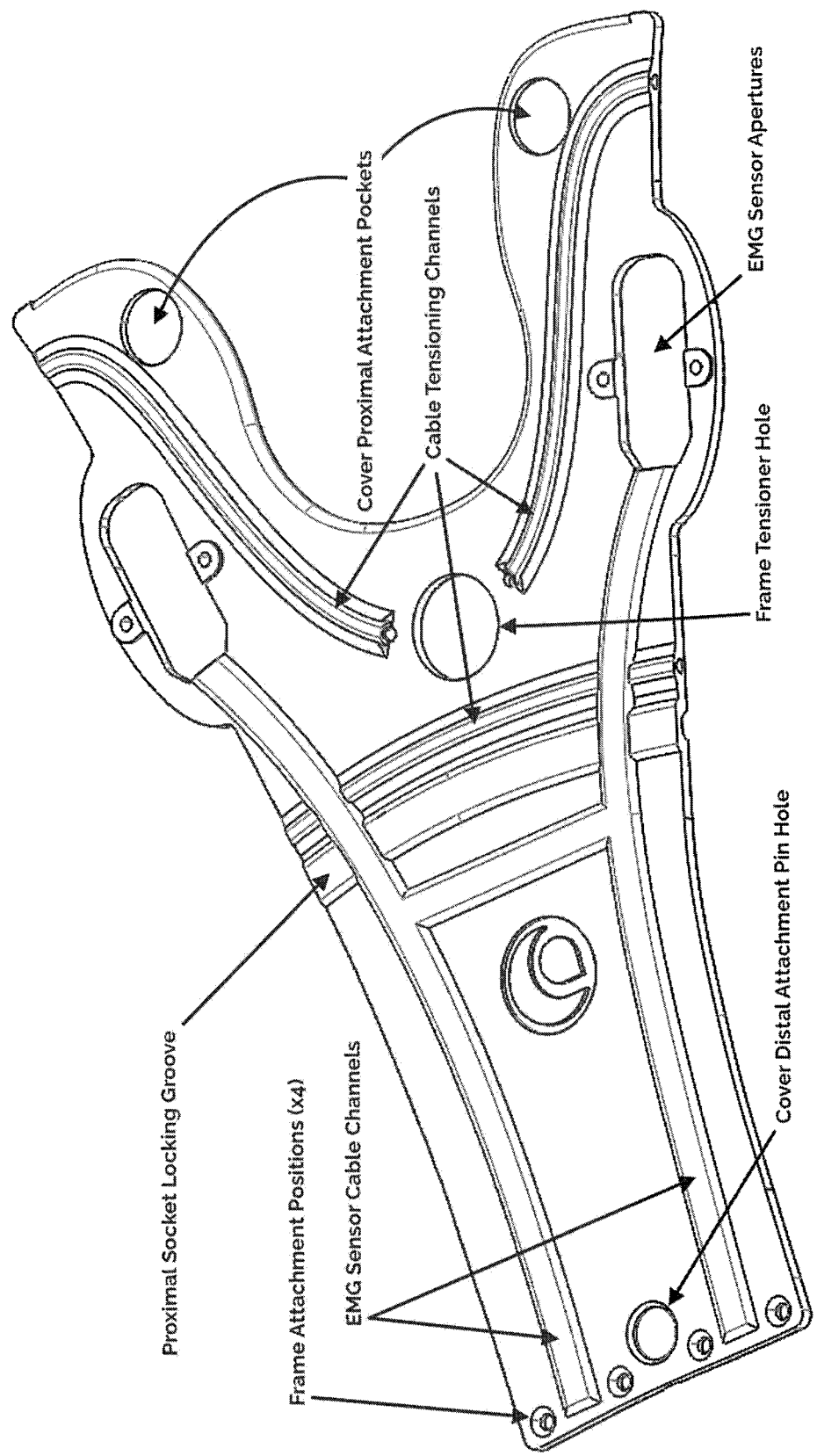
FIG. 9—Flat Upper Frame Nomenclature.
Figure 10:
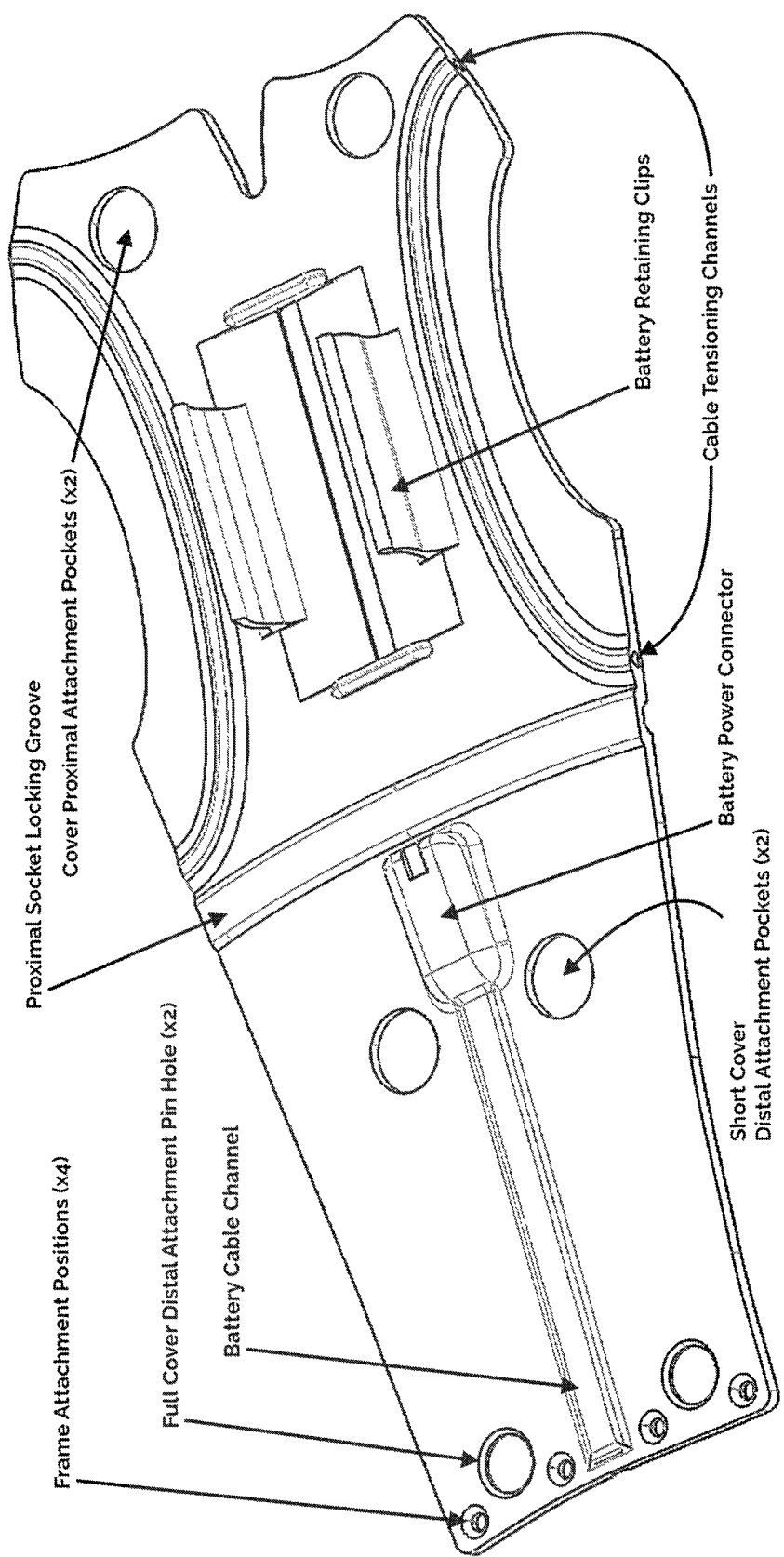
FIG. 10—Flat Lower Frame Nomenclature.
Figure 11:
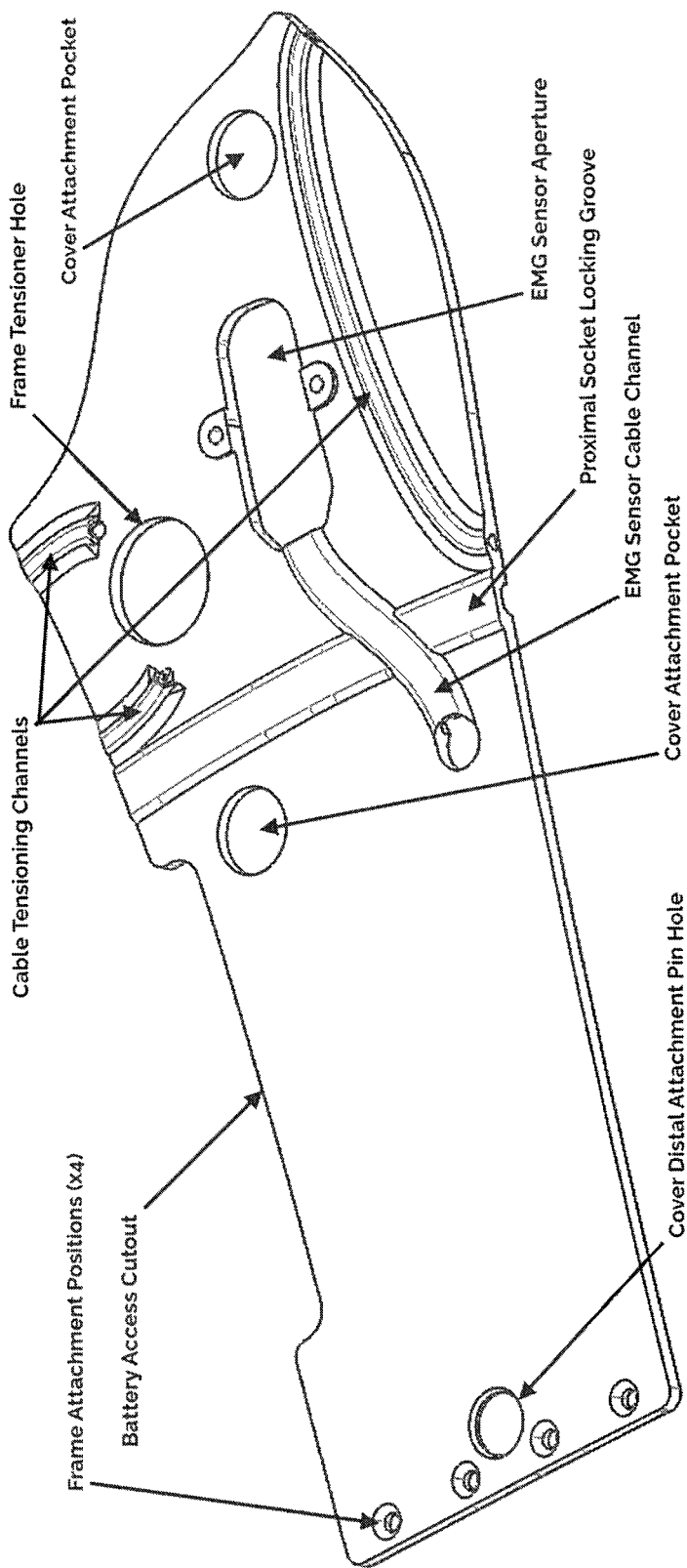
FIG. 11—Flat Left Frame Nomenclature.
Figure 12:
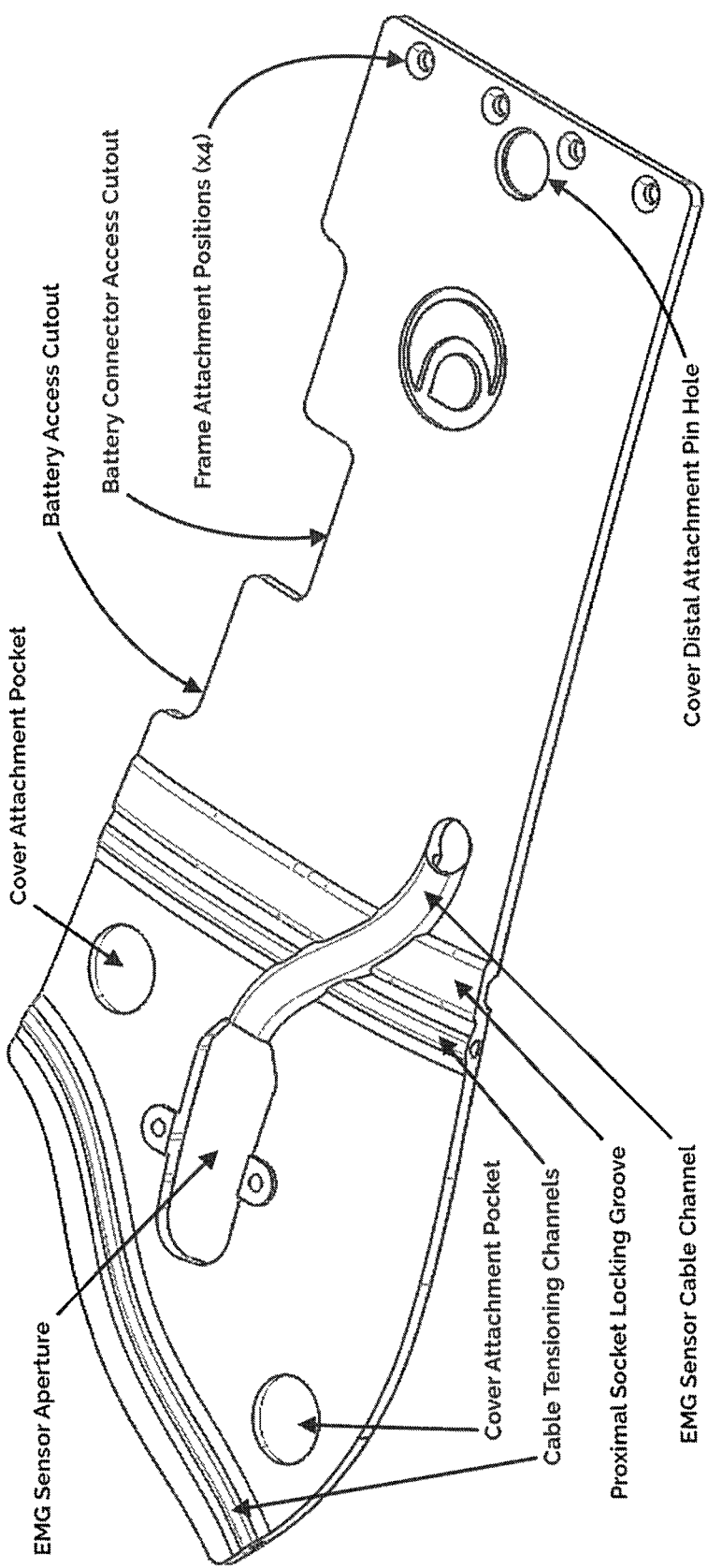
FIG. 12—Flat Right Frame Nomenclature.

One configuration has the battery pack attached externally to the arm and for this we split the frames into an upper and lower 125, 120 configuration (FIG. 7). A second configuration has the battery internal to the distal end of the arm and for this we split the frame into a left and right 225, 220 configuration (FIG. 8).

The frames are attached to the distal end of the socket by four self-tapping fasteners in each frame. A breakdown of the features in the frames of this embodiment can be seen in FIG. 9, FIG. 10, FIG. 11 and FIG. 12.

In this embodiment the frames are designed to be 3D printed flat and then thermoformed with heat to their desired shape on a 3D printed buck. An example of a thermoformed frame can be seen in FIG. 7 and in FIG. 19. This method achieves quick 3D print time and much stronger part due to the lamina direction. Forming a flat frame creates a lamina flow which follows the contours of the arm in a similar manner that a forged part creates a flowing grain direction that follows the shape of a component. To aid the thermoforming process, the forming buck is 3D printed, which is a copy of the patient's arm scan with some extra features. Location features are modelled into the buck to align important details in the frames such as EMG sensors, tensioner and cover attachment locations.

Figure 18:
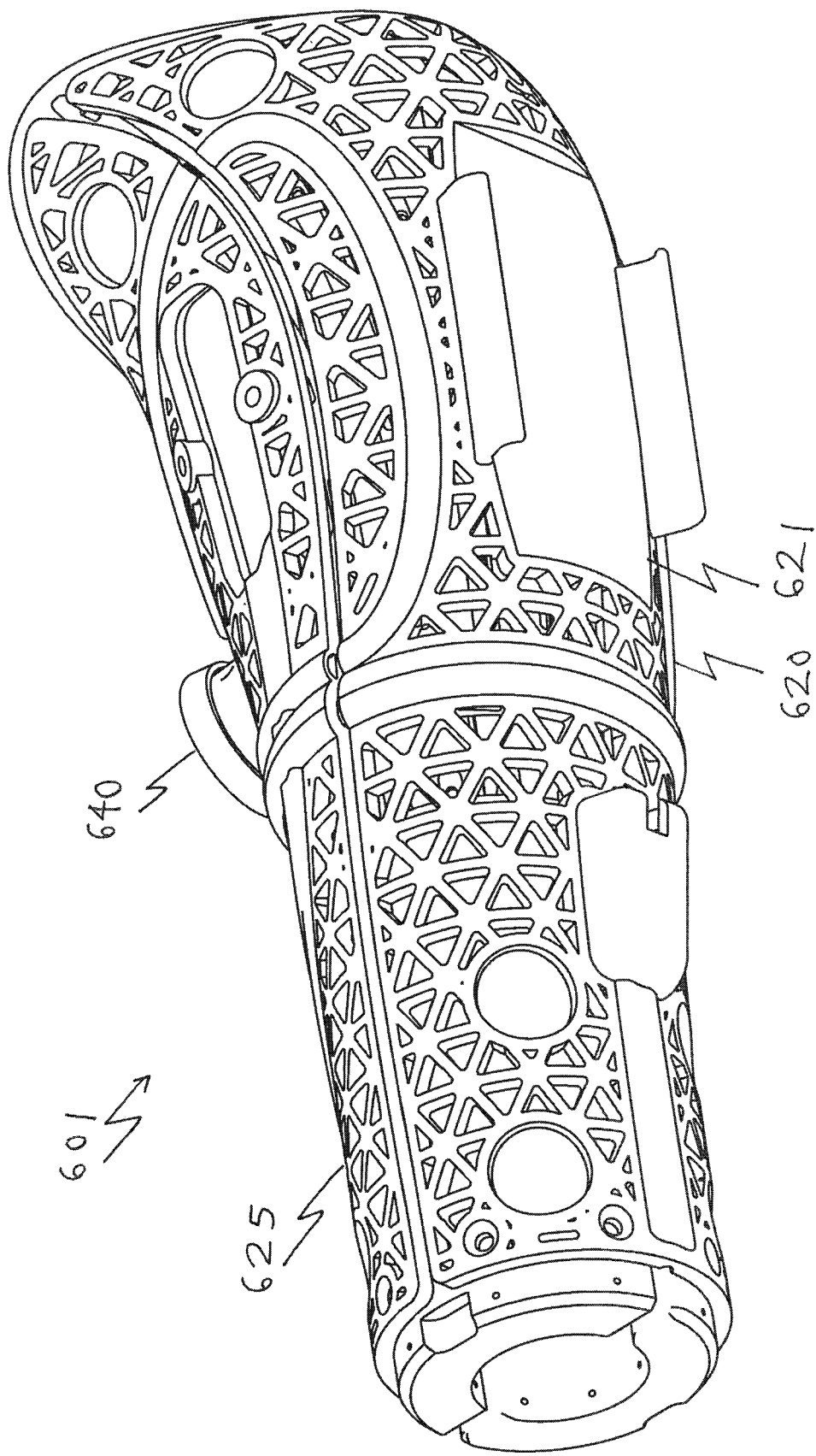
FIG. 18 to 22—socket/frame design.
Figure 19:
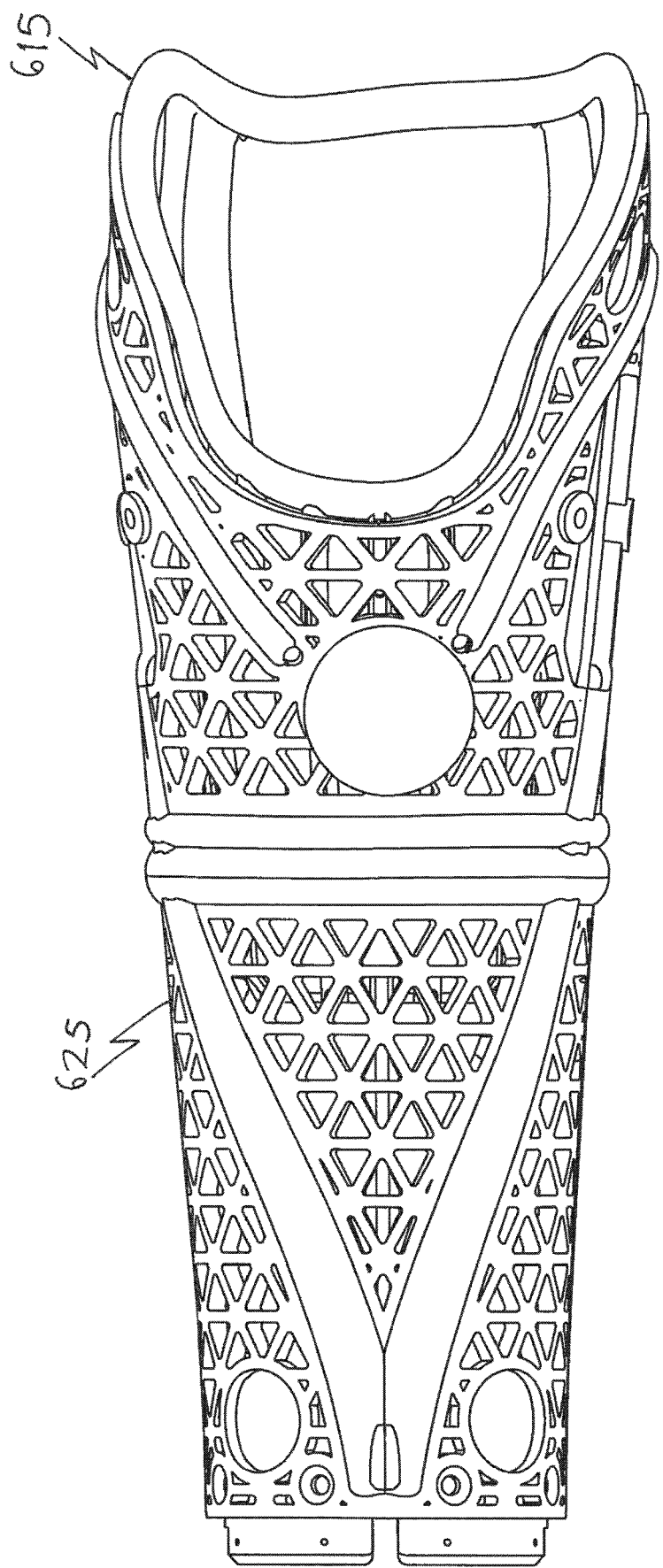
Figure 20:
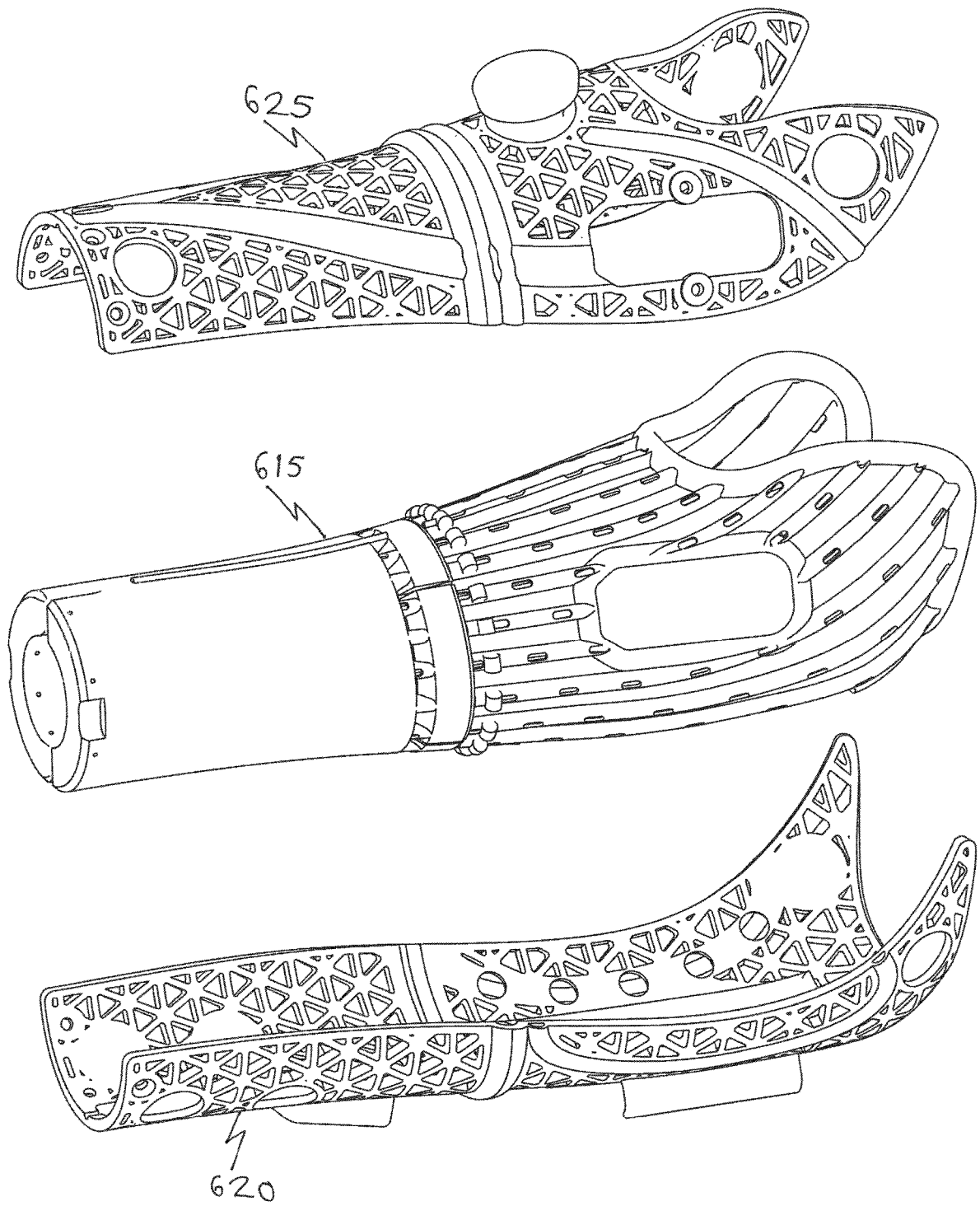
Figure 21:
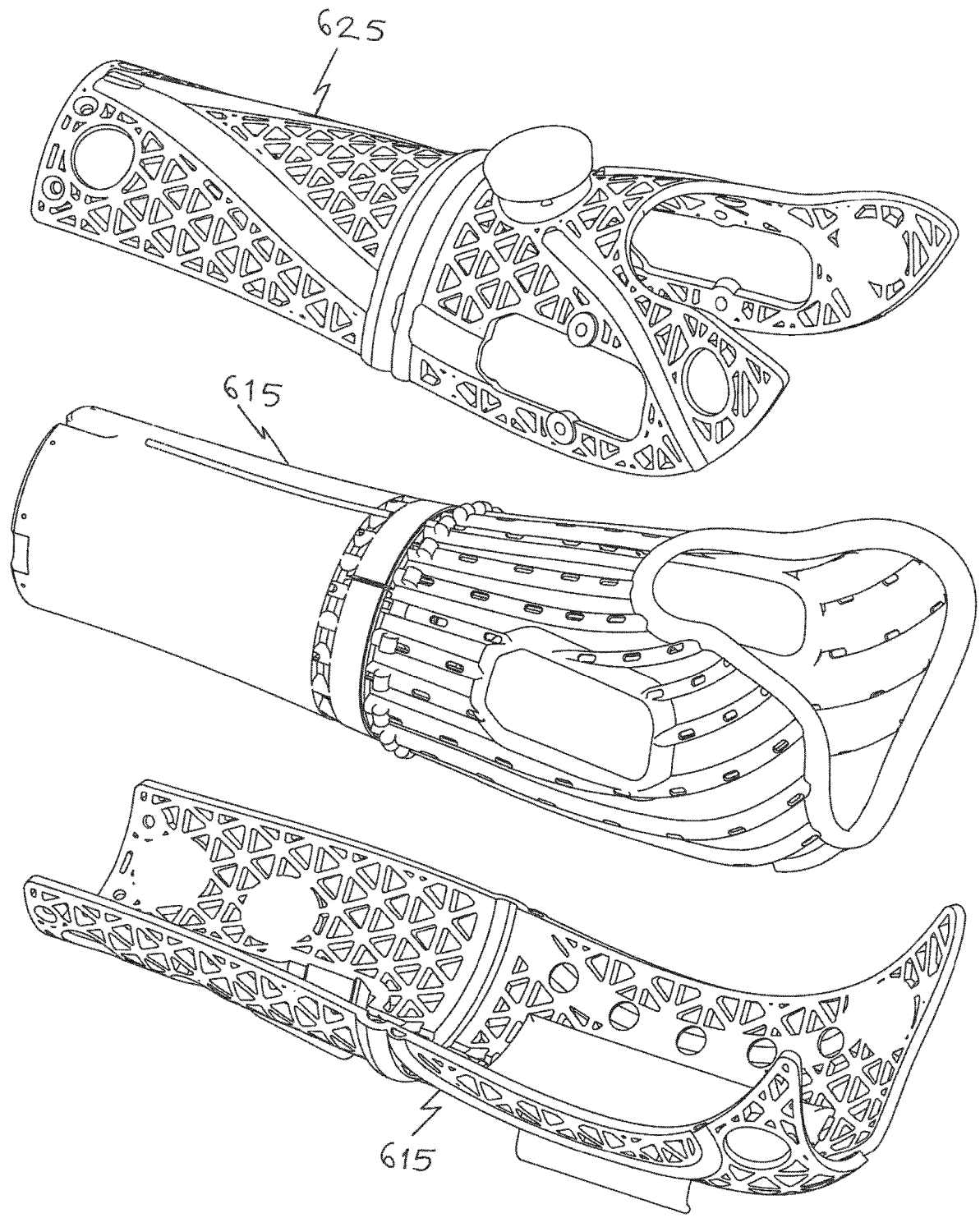
Figure 22:
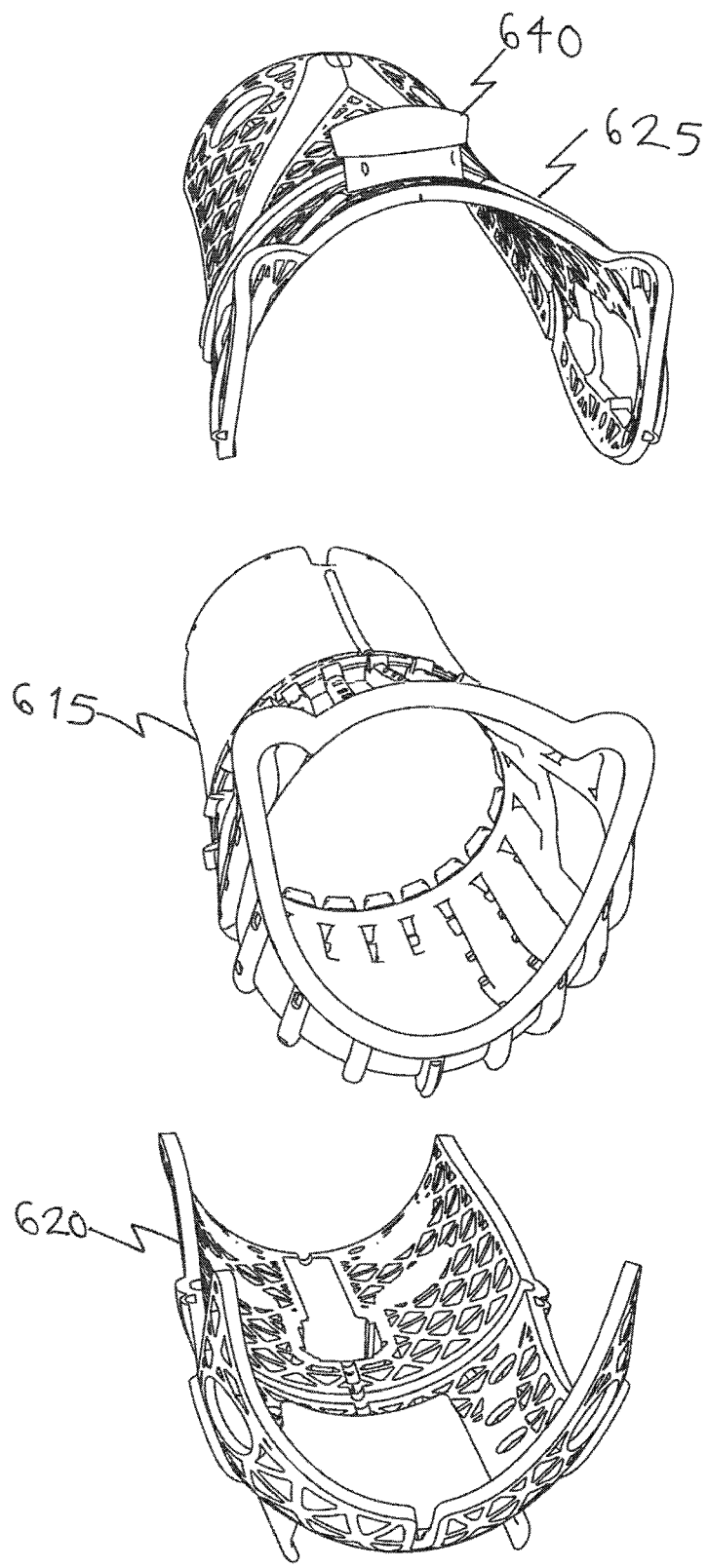
Figure 23:
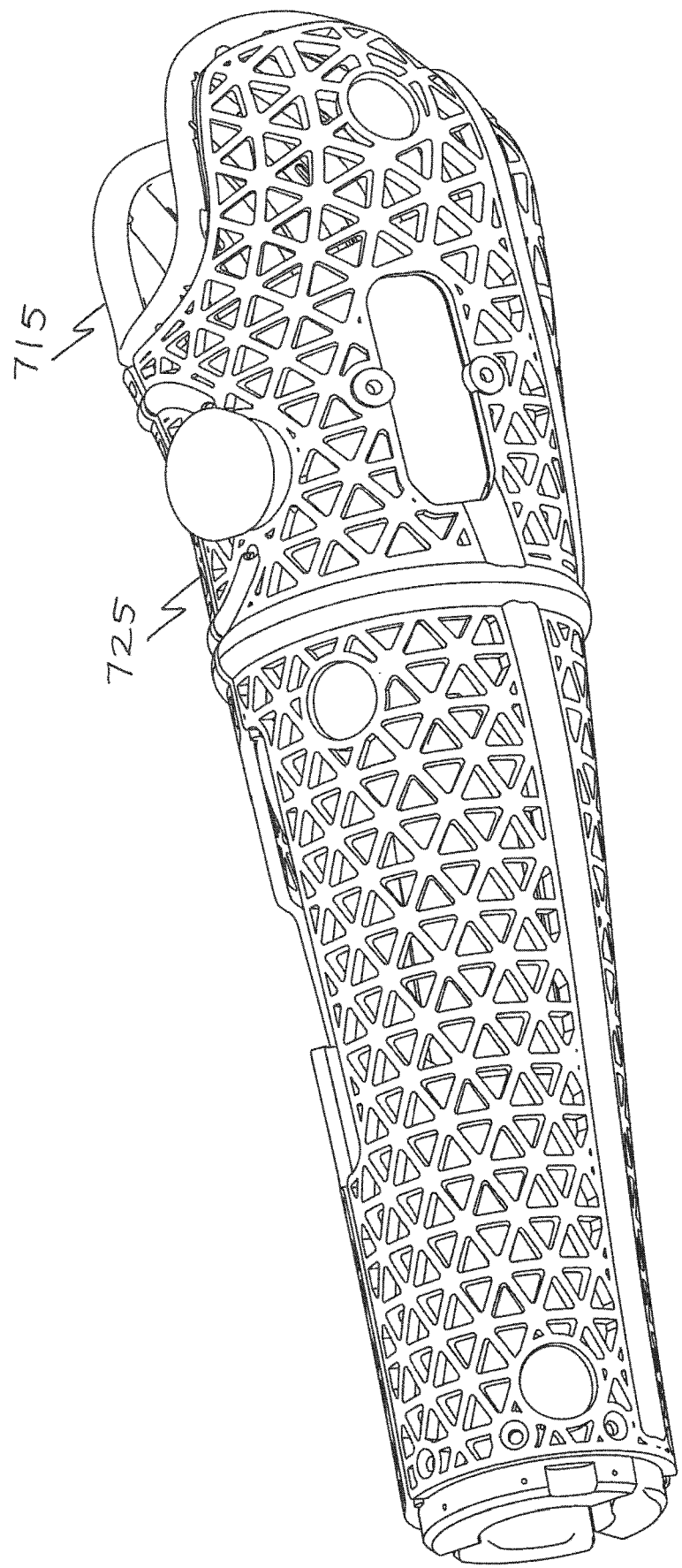
FIG. 23 to 29—socket/frame design.
Figure 24:
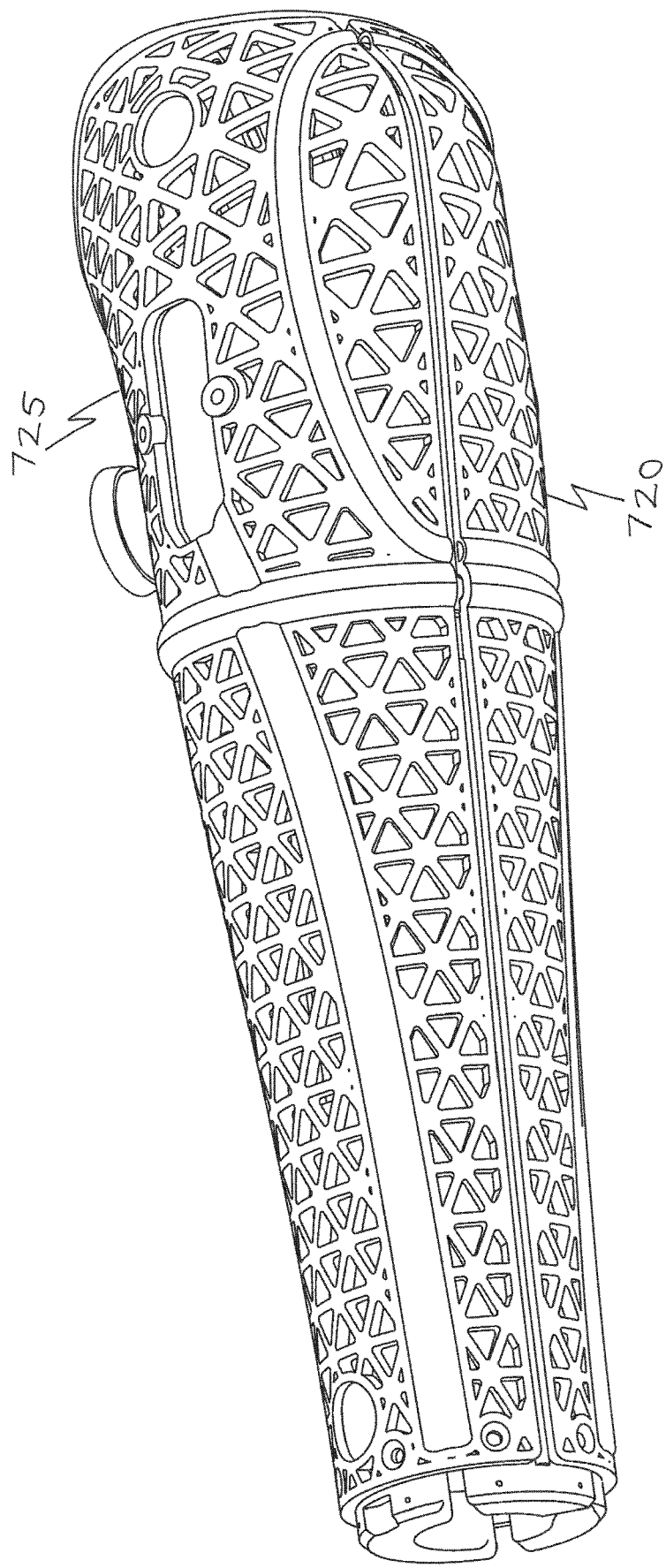
Figure 25:
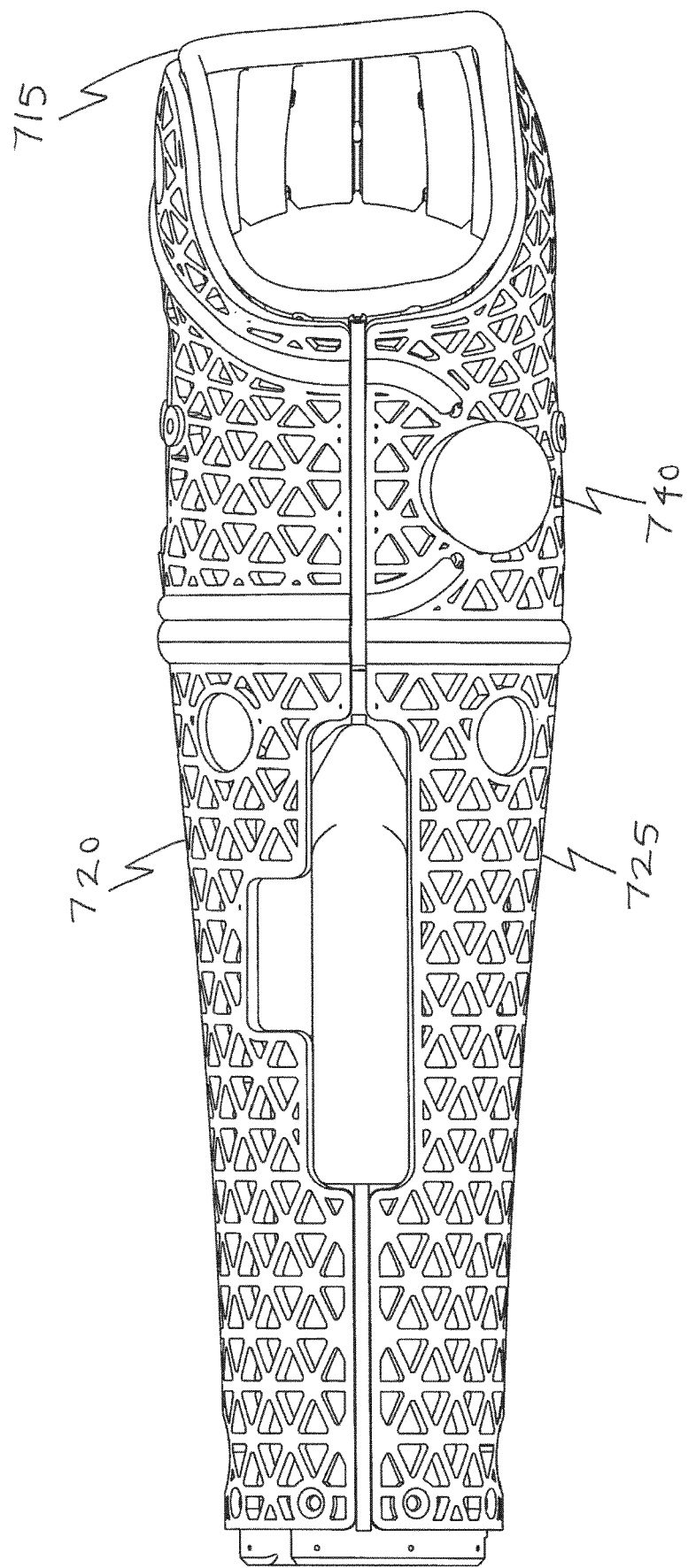
Figure 26:
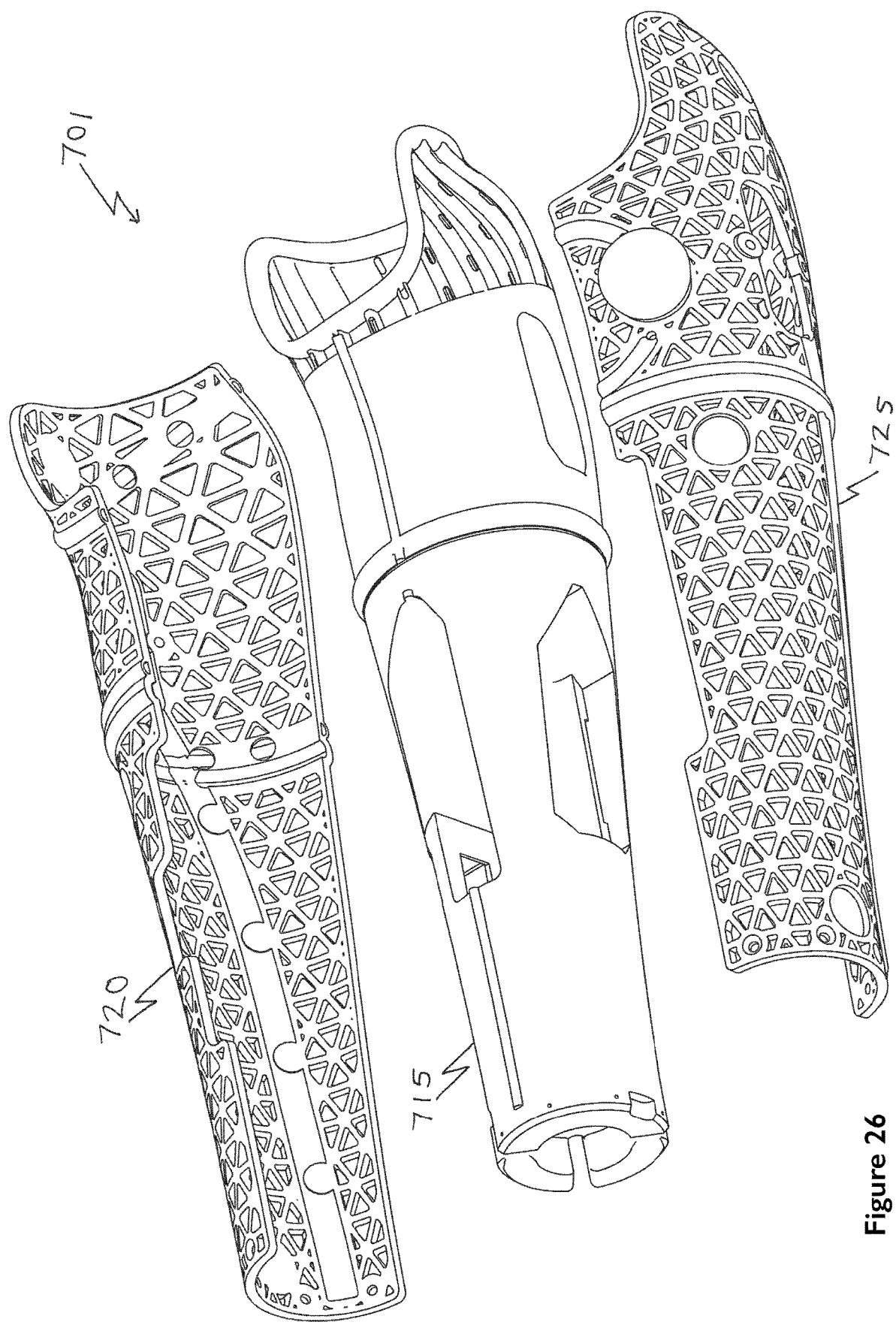
Figure 27:
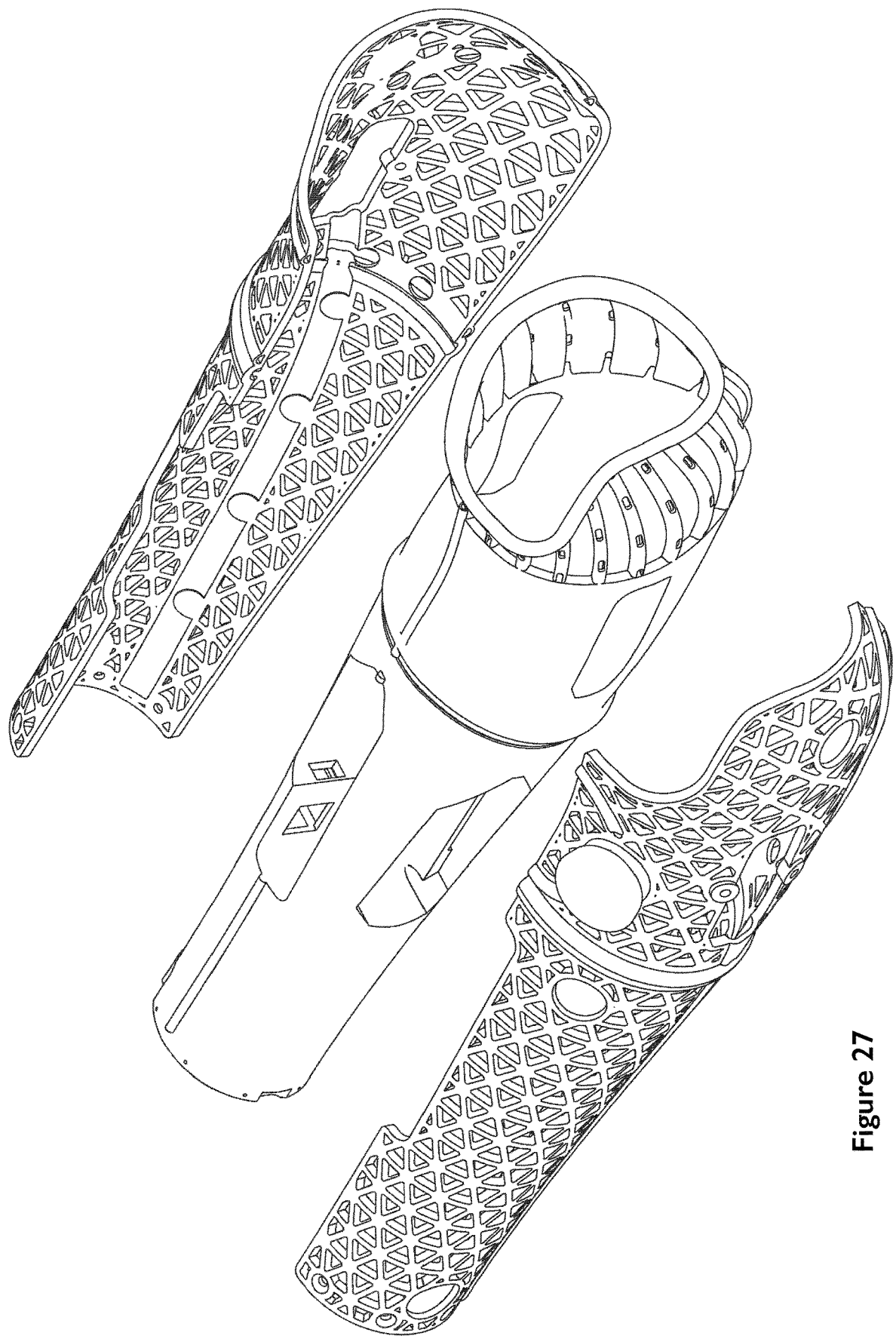
Figure 28:
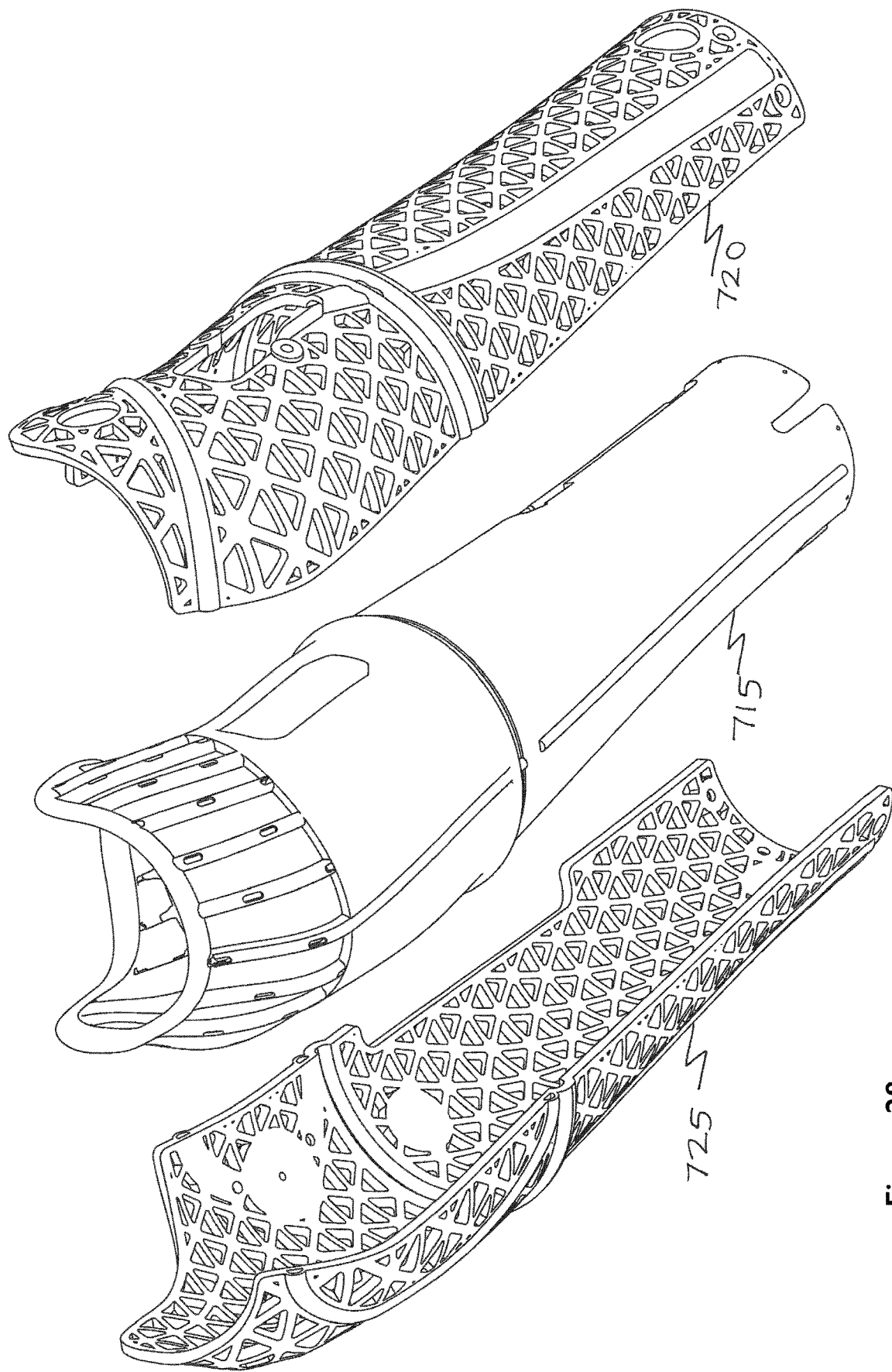
Figure 29:
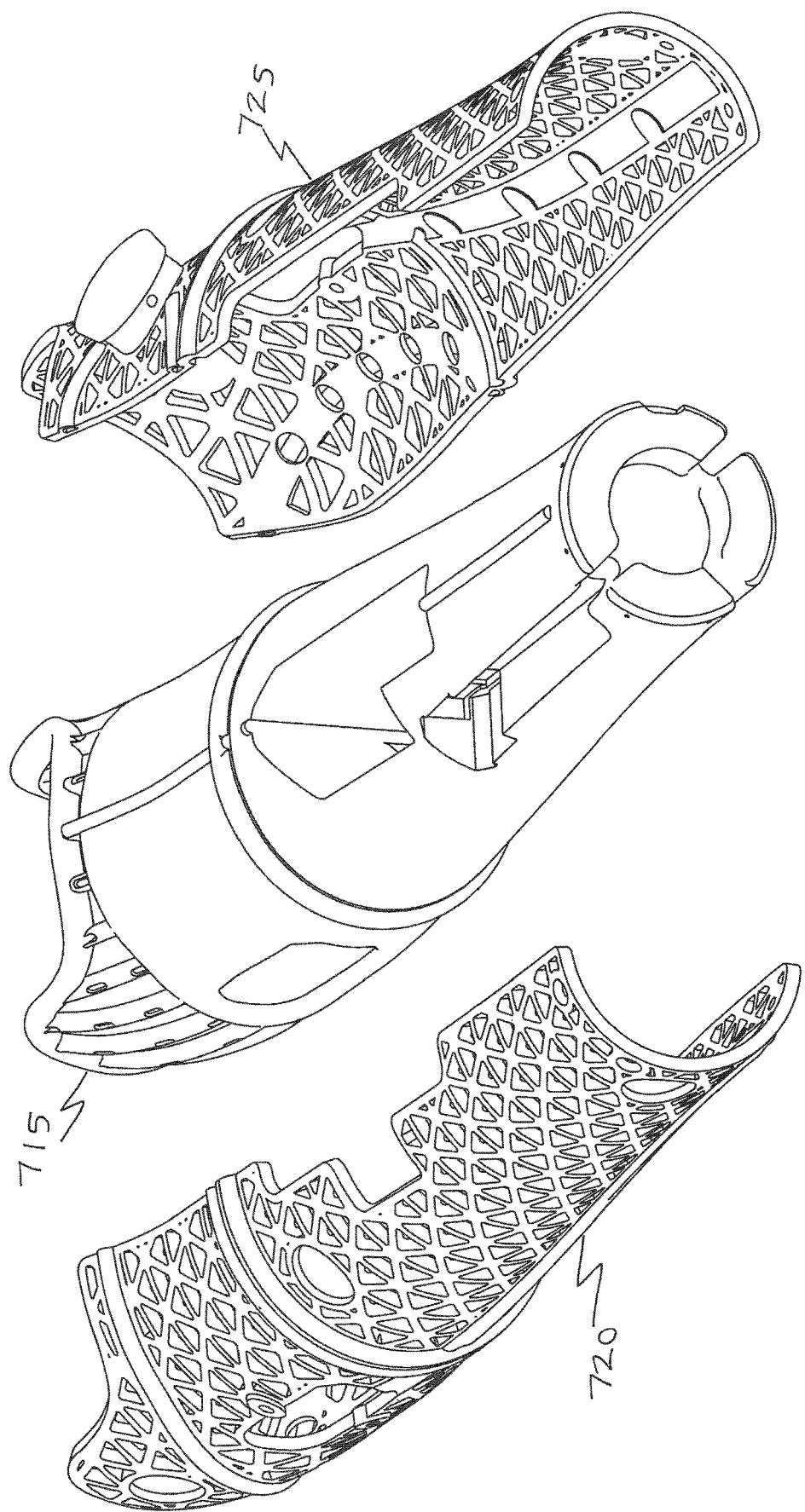

Another feature gained by FDM (Fused Deposition Modelling) printing flat is the ability to print the part without any upper and lower surfaces thus exposing the triangular mesh inside, this is known as "Open Core" as shown in FIG. 18 and FIG. 19. It creates a very lightweight, yet strong and faster to print component that allows a good amount of airflow through the frame to the internal socket. 3D printing this mesh in this way removes the time and complexity of modelling the ventilation in CAD. The mesh allows a bit more stretch and compression when working the frame over the forming bucks during thermoforming, reducing the risk of creasing. Large flat frames are also split proximal into and distal sub-components to allow them to fit on a 3D printing bed. The proximal and distal frames are joined by a friction stir weld before forming. The location of the joint is subtly hidden in the distal socket locking bead groove. On the underside of the frames are longitudinal grooves which line up with the socket ridges to help alignment during the thermoform phase and tensioning the socket.

All electrical cable routing is encapsulated in channels printed for the EMG sensors and captivated battery connector.

EMG Sensor Enclosure

Each EMG sensor assembly is bolted to the cutouts in the frames and aligns with the cutouts in the socket for through access to the skin.

Figure 13:
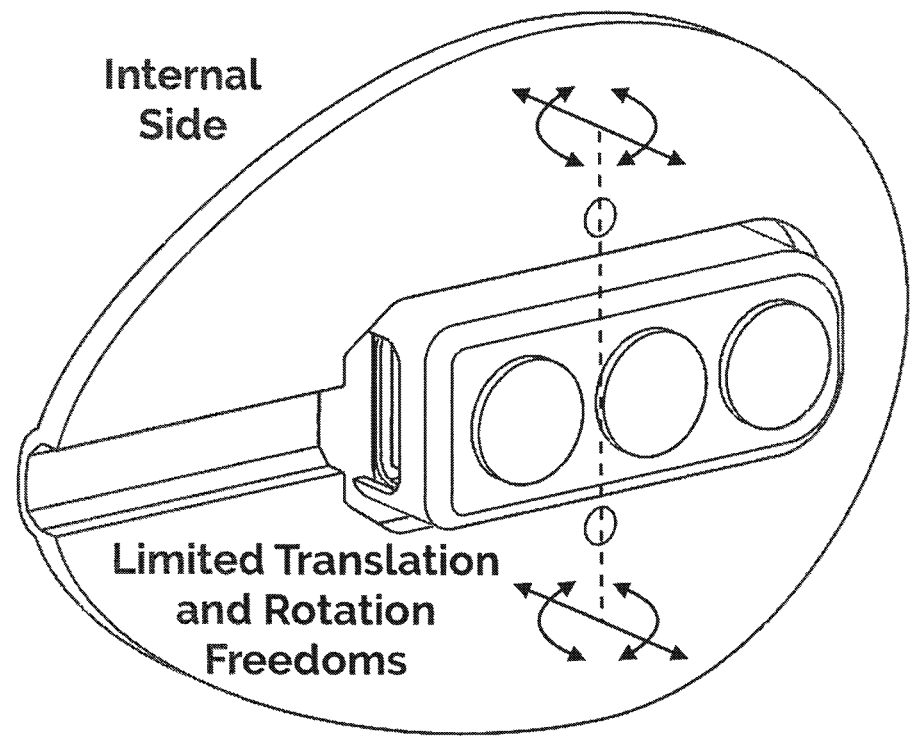
FIG. 13—EMG Sensor Assembly.
Figure 13:
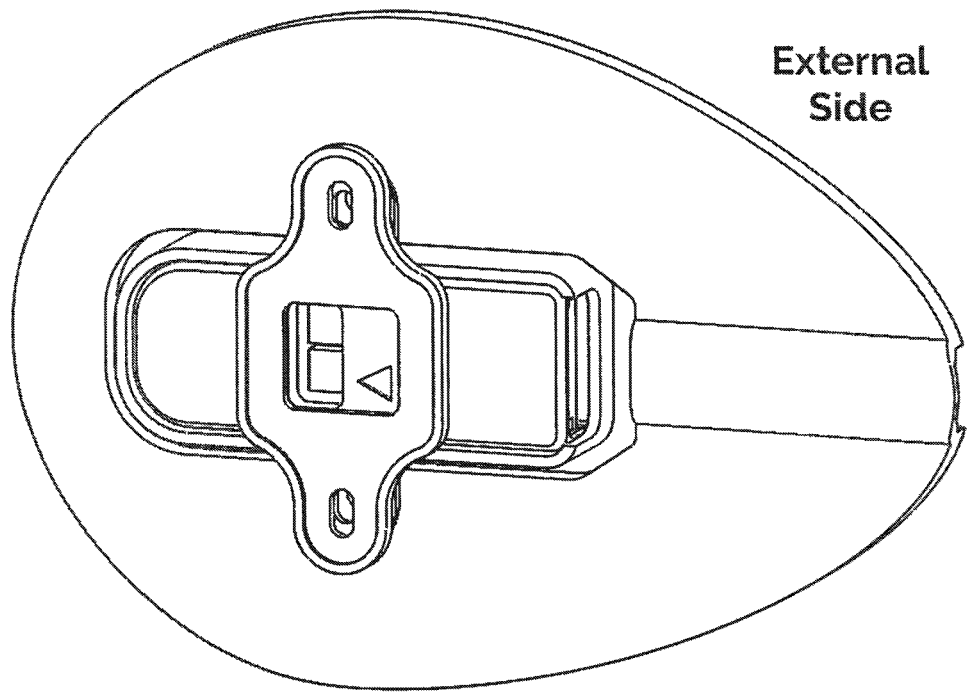
Figure 14:
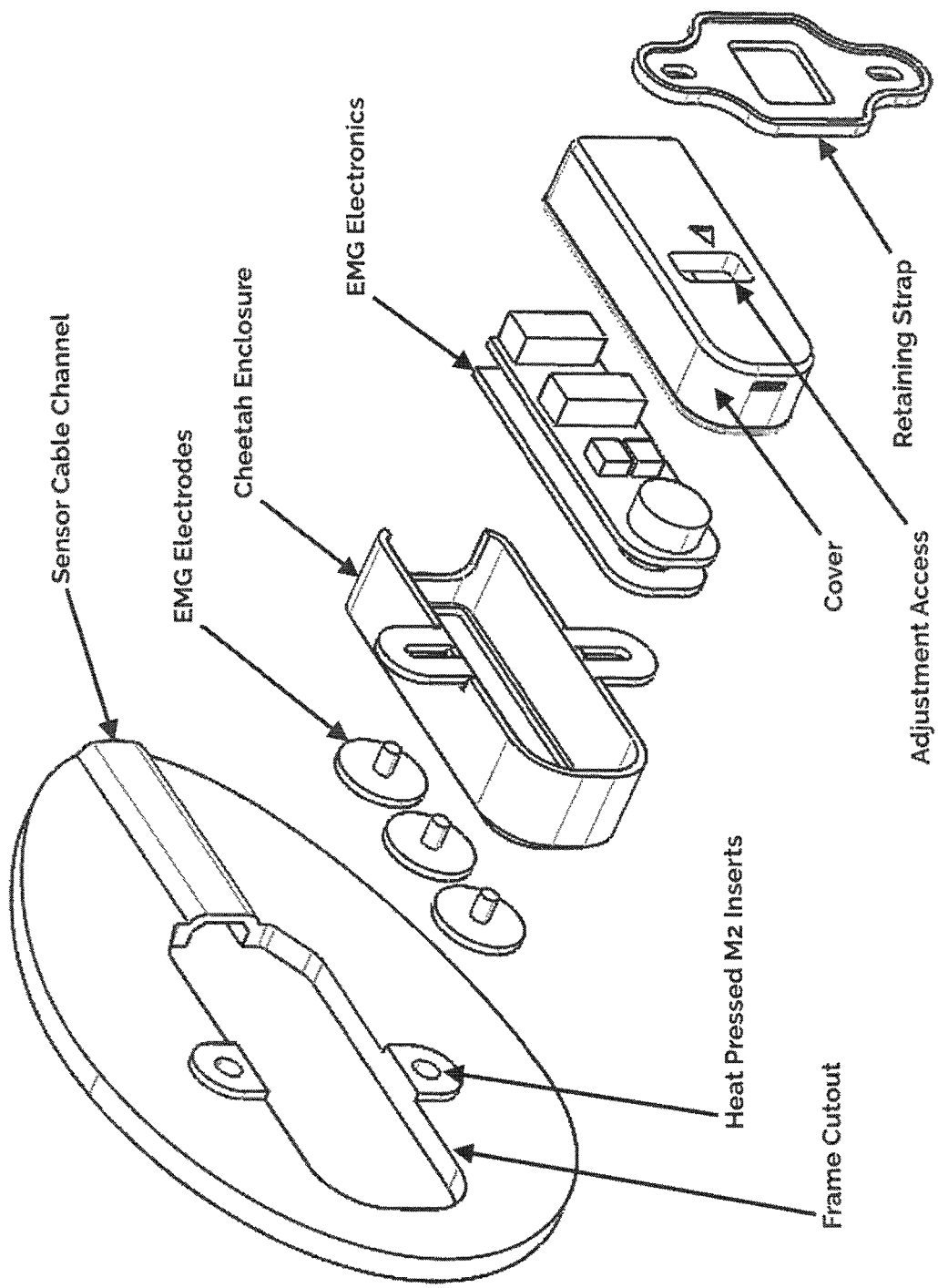
FIG. 14—EMG Sensor Assembly breakdown.

The assembly consists of five general components
1. Electrodes
2. Cheetah Enclosure
3. Sensor Board
4. Cover
5. Retaining Strap The assembly breakdown of these items can be seen in FIG. 13 and FIG. 14. The components that are in contact with the skin are the surgical stainless steel electrodes which are sandwiching a Cheetah printed barrier to keep the sensor board away from the skin. The barrier also encapsulates a rigid cover piece which is held in place by some printed Cheetah straps. The Cheetah straps and skin barrier component have eyelets in them to allow bolting to the frames. The frames have nut inserts heat pressed into them to facilitate accepting an M2 thread. The EMG assemblies are allowed to pivot and conform the shape of the skin to achieve a balanced contact. Tightening the panels with the tensioning system should push the electrodes further against the skin within their suspension range.

Cable Routing

The wiring loom has been designed in two parts to facilitate assembly and accommodate the user specific EMG sensors positions and battery pack. The EMG sensors are each fitted with two cable connectors so that the sensors can be daisy chained together. The order of the EMG sensors on the daisy chain can be changed to best suit the physical positioning of the EMG sensors on the arm. Excess cable length is accommodated by use of alternate routing paths and cable void spaces. The cable routing strategy enables a "one size fits all" cable set which can be sub-contract manufactured by specialist cable manufacturer.

Cable 1 connects the Universal Hand PCB to both the battery pack and the first EMG sensor in the daisy chain, via the wrist connector.

Cable 2 connects the first EMG sensor to the second in the daisy chain.

Both cables are protected from currents above the cable rating by a combination of three resettable thermal fuses of appropriate rating. Cable 1 battery pack lead is made with PTFE insulated 22AWG wire to specification MIL-DTL-16878/9 (TYPE ET), UL224 VW-1. This has been specified to provide a flexible small diameter wire that can carry the nine amp fault current that can be delivered by the battery. There are two conductors per battery connection, to respect the five amp per pin current rating of the wrist connector. This has the added benefit of providing redundancy and reducing the chance of power disconnects during wrist rotation. The battery lead is spiral formed on a mandrill so that it wraps around the cable branch that routes to the first EMG sensor; this prevents pulling on the wrist connector as the wrist rotates.

Both Cable 1 and Cable 2 EMG sensor leads are constructed using PVC insulated 28AWG UL style UL1061 wires. Both cables are covered in flexible polyolefin heat shrink tubing with UL224 VW-1 flammability rating. All connector plastics have UL94-V0 flammability rating. The more widely used Underwriters Laboratory standards UL224 & UL94 have been accepted as equivalent to or exceeding the IEC 60695 FV-1 flammability classification required by BS EN 60601-1. Both Cable 1 and Cable 2 are routed so that they do not come in contact with the users skin; therefore the insulation materials have been excluded from any skin sensitivity considerations.

Covers

Figure 15:
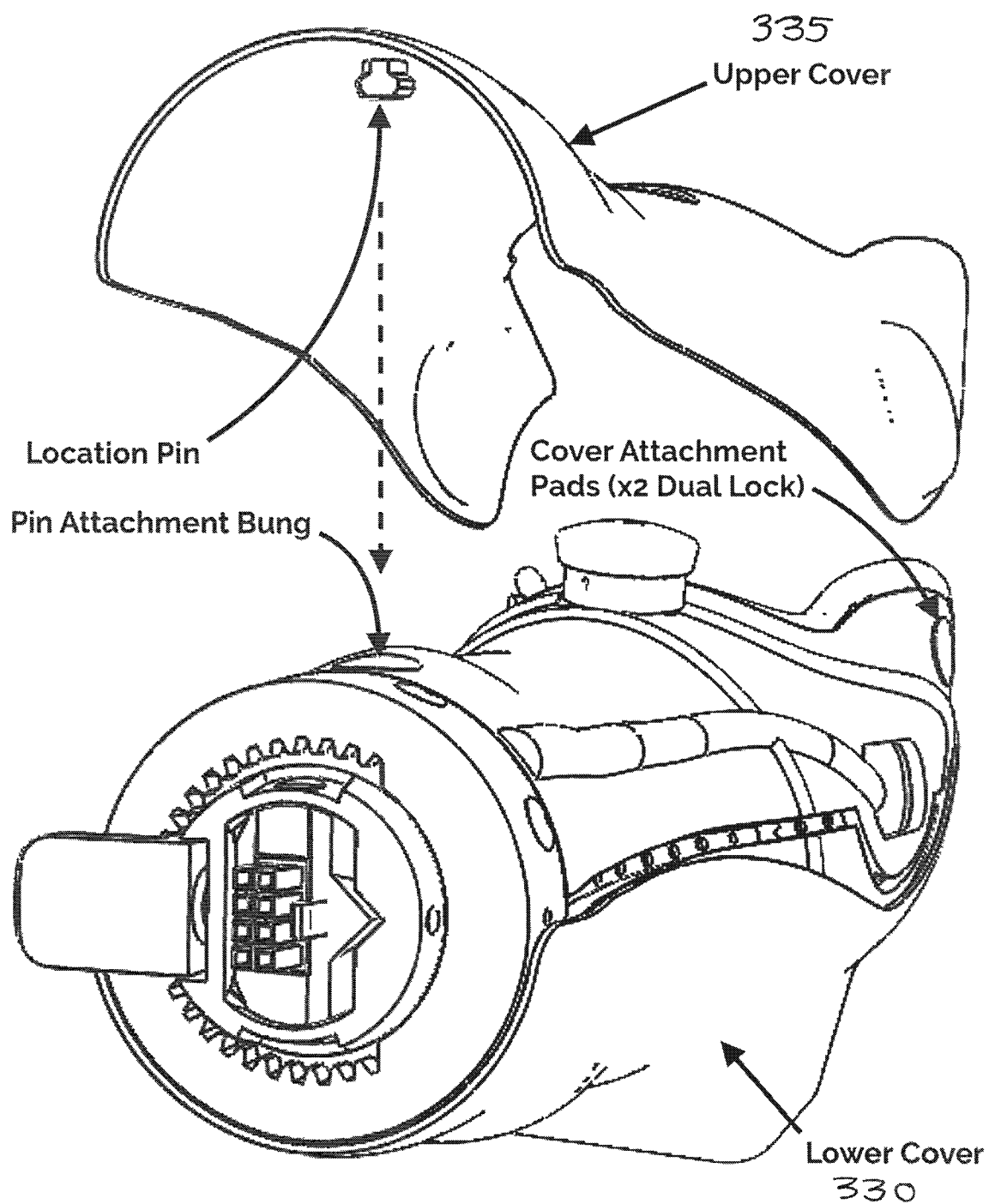
FIG. 15—Upper Cover Attachment.
Figure 16:
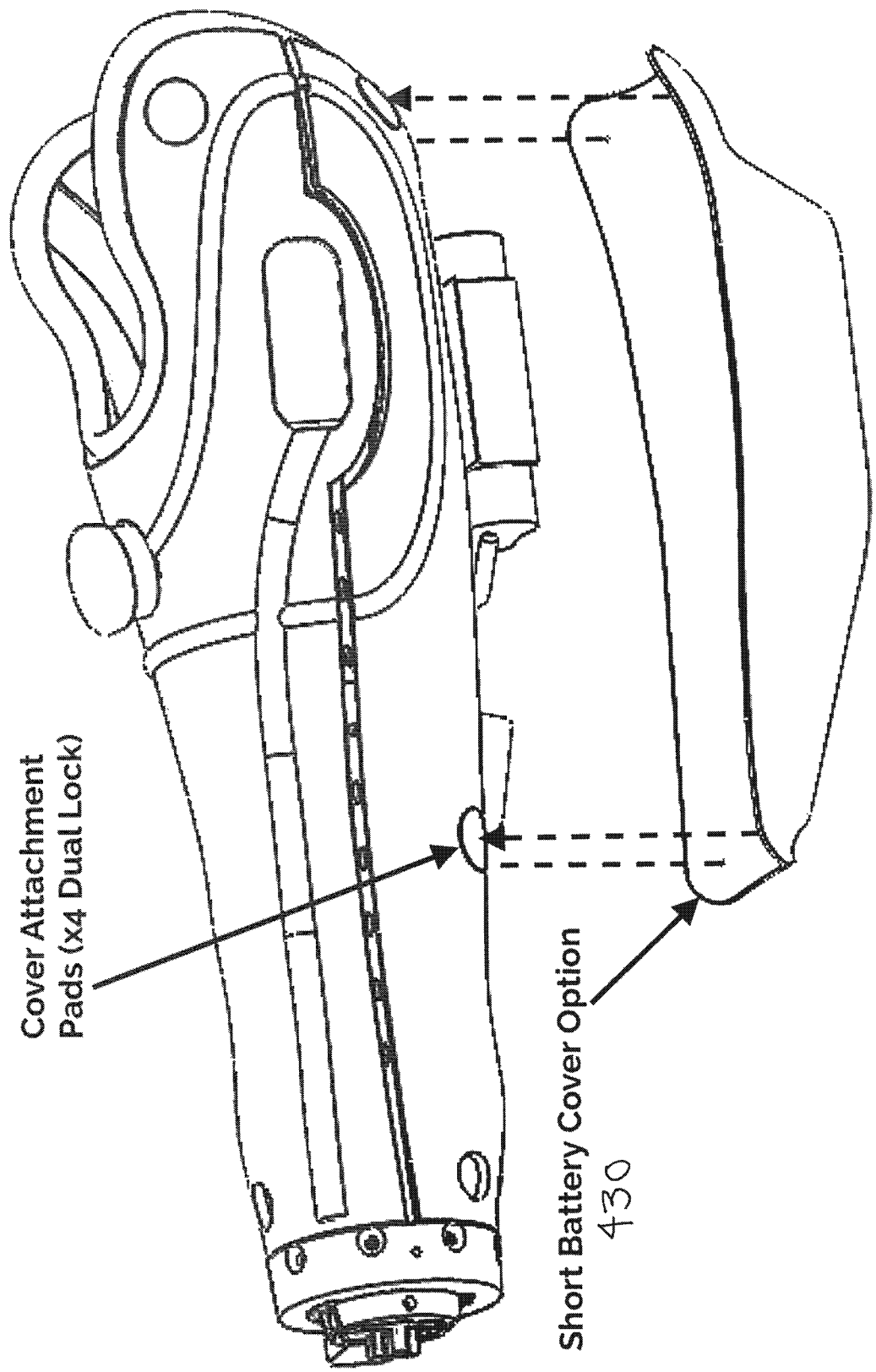
FIG. 16—Short Lower Cover Attachment.
Figure 17:
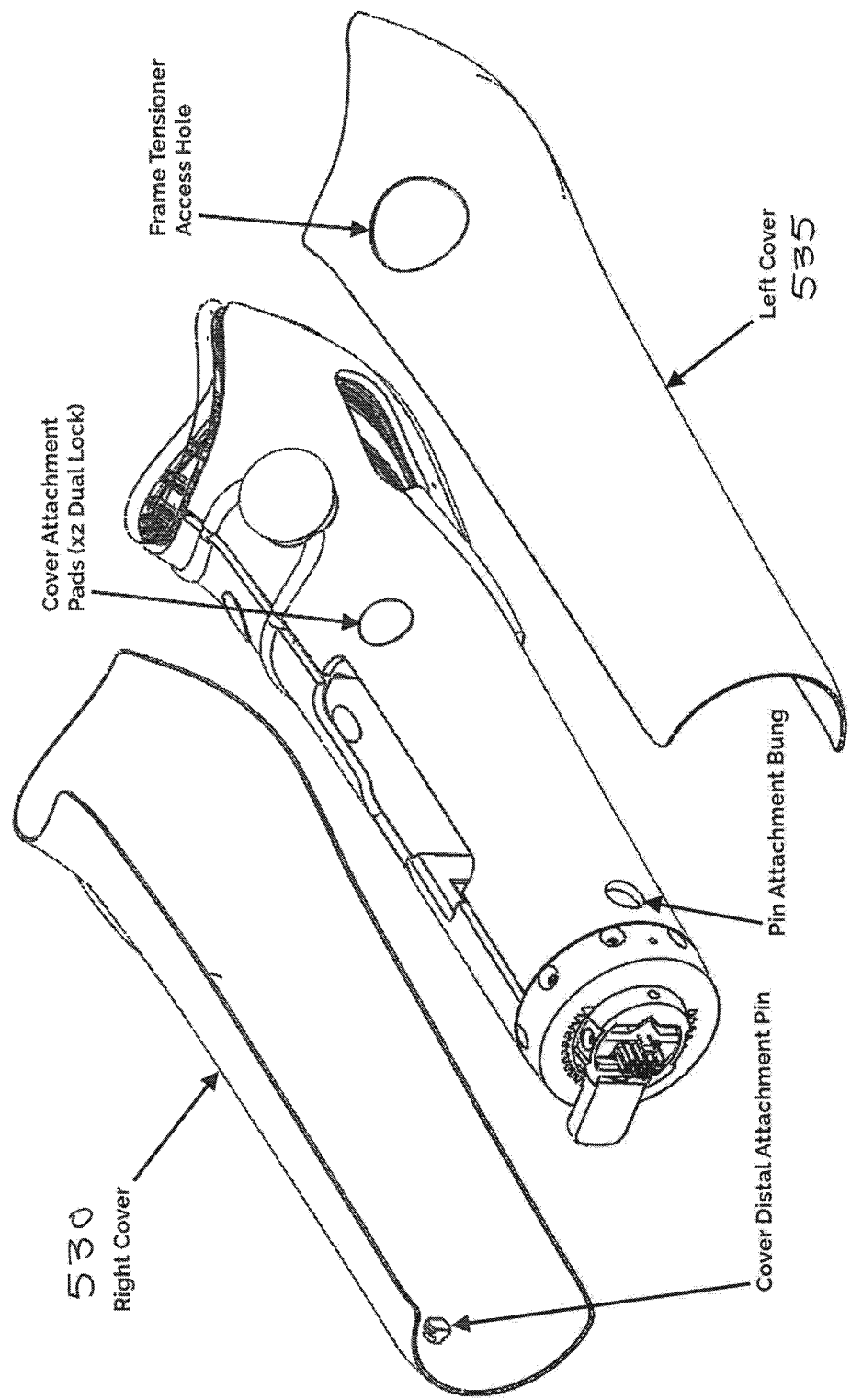
FIG. 17—Left/Right Cover Configuration.

Standard covers may be auto-generated as part of the CAD process. Two configurations which match the frames are shown: an upper/lower 335, 330 configuration (FIG. 15); or a left/right 535, 530 configuration (FIG. 17) for an external or internal battery respectively. The upper/lower configuration also has a short lower cover 430 (FIG. 16) supplied to protect the battery only, this is to enable the user to wear the arm with very minimal covers to reduce weight and increase airflow cooling. The covers are attached by push fit pins that are printed integral to the covers at the distal end (FIG. 15). The pins press into and are retained by a flexible Cheetah-based insert into the frames. At the proximal end of the covers there are two 3M branded Dual Lock pads affixed to the covers by glue. These pads locate with the similar pads attached to the frames and pressing them together forms a strong but removable bond. The short battery cover option does not have distal pins but four of the dual lock pads, one in each corner for fixation. In other embodiments magnets are used to attached the covers to the frame.

FIGS. 18 to 22 show an arm 601 formed according to a further embodiment. In this embodiment the two outer frame parts 620, 625 are formed already in the required shape, for example by selective laser sintering. The frame parts 620, 625 are both lattice-like, interlaced structures.

In this embodiment the frame part 625 is provided with the tightening dial 640 and the part 620 is provided with an external battery holder 621.

FIGS. 23 to 29 show an arm 701 formed according to a further embodiment. The arm 701 is similar to the arm 601, except that in this embodiment an internal battery compartment is formed in the inner liner/socket.

Material Choice

In some embodiments the printed parts are all made from two materials.

The rigid parts may, for example, be made from PLA, a biodegradable thermoplastic. PLA has been used in medical implant applications 1. The specific PLA used in the OB1 is produced by Filamentive. It is stated as being "essentially non-irritating to skin" in the Safety Data Sheet No PLA parts are in prolonged contact with the skin so this is considered low risk.

The flexible parts such as the ligaments and socket may, for example, be made from a TPU designed for 3D printing called "Cheetah" made by a company called Ninja Tek, a subsidiary of Fenner Drives. Cheetah is non-toxic, and certified for long term use in contact with skin.

The grip pads may, for example, be cast from Vytaflex 30 Urethane rubber.

Although illustrative embodiments of the invention have been disclosed in detail herein, with reference to the accompanying drawings, it is understood that the invention is not limited to the precise embodiments shown and that various changes and modifications can be effected therein by one skilled in the art without departing from the scope of the invention as defined by the appended claims and their equivalents.

The invention claimed is:

1. A prosthetic limb comprising:
   an inner socket formed from a flexible material and comprising a plurality of fluted channels, each of the plurality of fluted channels having a plurality of air flow openings in series with one another along the plurality of fluted channels, wherein the plurality of airflow openings extend only a thickness of the flexible material at the plurality of fluted channels; and
   an outer frame formed from a rigid material and having an open lattice structure.

2. A prosthetic limb as claimed in claim 1, further comprising a socket ridge extending from an end of the inner socket, wherein the socket ridge is received within a portion of the outer frame to prevent radial slip.

3. A prosthetic limb as claimed in claim 1, in which the outer frame is formed as two sections consisting of an upper section and a lower section or a left section and a right section.

4. A prosthetic limb as claimed in claim 1, and being formed by an additive manufacturing process.

5. A prosthetic limb as claimed in claim 1, wherein the plurality of airflow openings are in one or more channel walls of the plurality of fluted channels.

6. A prosthetic limb as claimed in claim 1, in which the outer frame has one or more attachment points for one or more removable covers.

7. A prosthetic arm as claimed in claim 1, in which the outer frame applies an adjustable clamping force on the inner socket.

8. A prosthetic limb as claimed in claim 1, in which the plurality of fluted channels are defined by one or more outwardly extending ridges and the plurality of air flow openings are formed in one or more of the one or more outwardly extending ridges.

9. An inner socket for a prosthetic limb comprising a plurality of fluted channels, each of the plurality of fluted channels having a plurality of airflow openings in series with one another along the plurality of fluted channels, wherein the inner socket is flexible and the plurality of airflow openings extend only a thickness of the plurality of fluted channels.

10. A prosthetic arm comprising an inner socket as claimed in claim 9, and further comprising an outer frame having an open lattice structure, wherein the outer frame has increased rigidity relative to the inner socket.

11. A prosthetic arm as claimed in claim 10, in which the outer frame is formed from a first and a second frame portion.

12. A prosthetic arm as claimed in claim 11, in which a removable cover portion is provided, a first cover portion being attachable to the first frame portion and a second cover portion being attachable to the second frame portion.

13. A prosthetic arm as claimed claim 10, further comprising a socket ridge extending from an end of the inner socket, wherein the socket ridge is received within a portion of the outer frame to prevent radial slip.

14. A prosthetic arm as claimed in claim 10, further comprising a hand.

15. A prosthetic arm as claimed in claim 10, in which the outer frame covers the inner socket.

16. A prosthetic arm as claimed in claim 10, in which the outer frame is formed as two sections consisting of an upper section and a lower section or a left section and a right section.

17. A prosthetic arm of claim 10, further comprising one or more cable entry slots at a distal end of the arm.

18. A prosthetic arm as claimed in claim 10, further comprising a tensioning system, wherein the tensioning system applies an adjustable clamping force on the inner socket via the outer frame.

19. An inner socket as claimed in claim 9, being formed as a one-piece article or being made from two sections.

20. An inner socket as claimed in claim 9, in which the plurality of fluted channels are defined by one or more outwardly extending ridges and the plurality of airflow openings are formed in one or more of the one or more outwardly extending ridges.

* * * * *